US012053439B2

(12) United States Patent
Pather et al.

(10) Patent No.: US 12,053,439 B2
(45) Date of Patent: *Aug. 6, 2024

(54) EDIBLE, SINGLE-EXTRACTION CURCUMA EXTRACTS

(71) Applicant: California Northstate College of Pharmacy, LLC, Elk Grove, CA (US)

(72) Inventors: Indiran Pather, Elk Grove, CA (US); Tibebe Zewdie Woldemariam, Elk Grove, CA (US)

(73) Assignee: CALIFORNIA NORTHSTATE COLLEGE OF PHARMACY, LLC, Elk Grove, CA (US)

( * ) Notice: Subject to any disclaimer, the term of this patent is extended or adjusted under 35 U.S.C. 154(b) by 401 days.

This patent is subject to a terminal disclaimer.

(21) Appl. No.: 17/198,102

(22) Filed: Mar. 10, 2021

(65) Prior Publication Data
US 2021/0267913 A1 Sep. 2, 2021

Related U.S. Application Data

(63) Continuation of application No. 16/264,301, filed on Jan. 31, 2019, now Pat. No. 10,973,778, which is a continuation of application No. 13/717,677, filed on Dec. 17, 2012, now Pat. No. 10,231,940, which is a continuation of application No. 13/590,188, filed on Aug. 21, 2012, now abandoned.

(51) Int. Cl.
A61K 31/12 (2006.01)
A61K 8/35 (2006.01)
A61K 8/9789 (2017.01)
A61K 8/9794 (2017.01)
A61K 36/23 (2006.01)
A61Q 17/04 (2006.01)

(52) U.S. Cl.
CPC ............... A61K 31/12 (2013.01); A61K 8/35 (2013.01); A61K 8/9789 (2017.08); A61K 8/9794 (2017.08); A61K 36/23 (2013.01); A61Q 17/04 (2013.01)

(58) Field of Classification Search
None
See application file for complete search history.

(56) References Cited

U.S. PATENT DOCUMENTS

| | | | |
|---|---|---|---|
| 5,152,983 | A | 10/1992 | Nambudiry et al. |
| 5,861,415 | A | 1/1999 | Majeed et al. |
| 7,763,289 | B2 | 7/2010 | Bommarito |
| 7,968,115 | B2 | 6/2011 | Kurzrock et al. |
| 8,153,172 | B2 | 4/2012 | Antony |
| 8,815,220 | B2 | 8/2014 | Pather et al. |
| 10,231,940 | B2 | 3/2019 | Pather et al. |
| 10,973,778 | B2 | 4/2021 | Pather et al. |
| 2004/0121031 | A1 | 6/2004 | Majeed et al. |
| 2006/0045928 | A1 | 3/2006 | Oshiro |
| 2007/0105130 | A1 | 5/2007 | D'Andrea et al. |
| 2007/0281045 | A1 | 12/2007 | Tripp et al. |
| 2010/0105644 | A1 | 4/2010 | Varani et al. |
| 2012/0052095 | A1 | 3/2012 | Chaniyilparampu et al. |
| 2012/0177757 | A1 | 7/2012 | Hidmi et al. |
| 2014/0056828 | A1 | 2/2014 | Pather et al. |

FOREIGN PATENT DOCUMENTS

| | | |
|---|---|---|
| CN | 1626068 | 6/2005 |
| EP | 1825845 | 8/2007 |
| JP | 2003/137799 | 5/2003 |
| JP | 2005/194246 | 7/2005 |
| JP | 2007/320864 | 12/2007 |
| WO | WO2005/097152 | 10/2005 |
| WO | WO2007/043058 | 4/2007 |
| WO | WO2007/109210 | 9/2007 |
| WO | WO2010/045577 | 4/2010 |
| WO | WO2010/070675 | 6/2010 |
| WO | PCT/US2013/055499 | 8/2013 |

OTHER PUBLICATIONS

European search report for EP 13830806.9, Jul. 1, 2015, California Northstate College of Pharmacy, LLC.
European search report for EP 19214450.9, Jul. 1, 2015, California Northstate College of Pharmacy, LLC.
International search report for PCT/US2013/055499, Aug. 19, 2013, California Northstate College of Pharmacy, LLC. et al.
Written Opinion of International search authority for PCT/U82013/055499, Nov. 27, 2013, California Northstate College of Pharmacy, LLC. et al.
Anand, P. et al. Bioavailability of curcumin: problems and promises. Mol pharmaceutics 4(6): 807-818 (2007).
Anand, P. et al. Design of curcumin-loaded plga nanoparticles formulation with enhanced cellular uptake, and increased bioactivity in vitro and superior bioavailability in vivo. Biochem pharmacol 79(3): 330-338 (Feb. 1, 2010).
Anuchapreeda, et al., Preparation of lipid Nanoemulsions Incorporation Curcumin for Cancer Therapy, Journal of Nanotechnology 2012:1-11, 2012.
Austrilian Patent Office; 3$^{rd}$ party observation dated Nov. 12, 2015 (directed to only compositions and methods of treatment, and Not the methods of making).

(Continued)

Primary Examiner — Terry A McKelvey
Assistant Examiner — Catheryne Chen
(74) Attorney, Agent, or Firm — Brian S. Boyer; SYNDICATED LAW, PC

(57) ABSTRACT

Methods of making safe extracts of *Curcuma* are provided. The processes provided include methods that use an extraction solvent that is at least substantially non-toxic and useful also as a pharmaceutically acceptable carrier in liquid dosage forms. The processes can produce a significantly higher yield from a single extraction than the state-of-the-art processes. For example, liquid dosage forms can be produced directly from the extraction process without requiring removal of the extraction solvent, reducing complexity and cost of processing over the state-of-the-art. Methods of making microemulsions and nanoemulsions are also provided to enhance the bioavailability and stability of the extracts.

36 Claims, 3 Drawing Sheets

(56) References Cited

OTHER PUBLICATIONS

Bong, P.H. Spectral and photophysical behaviors of curcumin and curcuminoids. Bull Korean chem soc 21(1): 81-86 (2000).
Braga, M. E. M., et al., Comparison of yield, composition, and antioxidant activity of turmeric (*Curcuma longa* l.) extracts obtained using various techniques. Journal of Agricultural and Food Chemistry, American Chemical Society 51(22): 6604-6611(2003).
Brezova V. et al. Reactive oxygen species produced upon photoexcitation of sunscreens containing titaniumdioxide (an EPR study). J photochemistry and photobiology b: biology 79(2): 121-134 (May 13, 2005).
Bisht S. et al. Systemic delivery of curcumin: $21^{st}$ century solutions for an ancient conundrum. Curr drug discov technol September 6(3): 192-199 (2009).
Cartiera, M.S. et al. Partial correction of cystic fibrosis defects with plga nanoparticles encapsulating curcumin. Mol pharm 7(1): 86-93 (Feb. 1, 2010).
Çikrikçi, S. et al. Biological activity of curcuminoids isolated from curcuma longa. Rec nat prod 2(1): 19-24(2008).
Chen, Shih-Shin. The inhibition effect of curcumin on the melanin formation by melanocytes and the application to cosmetics. NTOU: Dept. of Food Science. (2006) Abstract Only.
Cho, J.W. et al. Curcumin inhibits the expression of COX-2 in UVB-irradiated human kerat inocytes (HaCaT) by inhibiting activation of AP-1: p38 MAP kinase and JNK as potential upstream targets. Experimental and molecular medicine 37(3): 186-192 (2005).
Epstein, J. et al. Curcumin as a therapeutic agent: The evidence from in vitro, animal and human studies. Br J Nutr 103(11): 1545-1557 (Jun. 2010). [online] [retrieved on May 14, 2013] URL: http://journals.cambridge.org/action/displayAbstract?fromPage=online&aid=7793062.
Farmer, K.C. et al. Sun exposure, sunscreens, and skin cancer prevention: a year-round concern. Ann pharmacother 30(6): 662-673 (Jun. 1996).
Goel, A. et al. Curcumin as "curecumin": from kitchen to clinic. Biochem pharmacol 75(4): 787-809 (Feb. 15, 2008).
Gorham E.D. et al. Do sunscreens increase risk of melanoma in populations residing at higher latitudes? Annals of epidemiology 17(12): 956-963 (Dec. 2007).
Guidance for Industry: Estimating the maximum safe starting dose in initial clinical trials for therapeutics in adult healthy volunteers. U.S. Department of Health and Human Services, Food and Drug Administration, Center for Drug Evaluation and Research (CDER). Pharmacology and Toxicology (Jul. 2005). [online] [retrieved on Aug. 8, 2015] URL: http://www.fda.gov/downloads/drugs/ . . . /Guidances/UCM078932.pdf.
Huang, M.T. et al. Effects of curcumin, demethoxycurcumin, bisdemethoxycurcumin and tetrahydrocurcumin on 12-o-tetradecanoylphorbol-13-acetateinduced tumor promotion. Carcinogenesis 16(10): 2493-2497 (Oct. 1995).
Huang, M.T. et al. Inhibitory effects of curcumin on tumorigenesis in mice. J cell biochem Suppl 27: 26-34 (1997).
Jansirani, D, et al., Comparative evaluation of various extraction methods of curcuminoids from Curcuma longa, JCHPS Special Issue 4:286-288 (Dec. 2014).
Jurenka, J.S. Anti-inflammatory properties of curcumin, a major constituent of curcuma longa: a review of preclinical and clinical research. Altern med rev 14(2): 141-53 (Jun. 2009).
Katsuyama, Y. et al. Production of curcuminoids by *Escherichia coli* carrying an artificial biosynthesis pathway. Microbiology 154: 2620-2628 (2008).
Khopde, M. et al. Free radical scavenging ability and antioxidant efficiency of curcumin and its substituted analogue. Biophysical chemistry 80(2): 85-91. (Aug. 9, 1999).
Kulkarni, S.J. et al., Extraction and purification of curcuminoids from Turmeric (*Curcuma longa* L.), International Journal of Pharmacology and Pharmaceutical Technology (IJPPT), 1(2):81-84(2012).
Kumar, A. et al. Conundrum and therapeutic potential of curcumin in drug delivery. Crit rev ther drug carrier syst. 27(4): 279-312 (2010).
Kurita, T., et al., Novel curcumin oral delivery systems. Anticancer Research. p. 2807-2822 (2013) URL: http://ar.iiarjournals.org/content/33/7/2807.full.pdf.
Li, S. et al. Chemical composition and product quality control of turmeric (*Curcuma longa* L.), Pharmaceutical Crops 2:28-54 (2011).
Lin, X. L. et al. Determination of curcumins in turmeric by micellar electrokinetic capillary chromatography. Canadian journal of analytical sciences and spectroscopy 51(1): 35-42 (2006).
Masuda, T. et al. Antioxidative curcuminoids from rhizomes of curcuma xanthorrhiza. Phytochemistry 31(10): 3645-3647 (Oct. 1992).
Median Lethal Dose: [Online] [retrieved on Aug. 8, 2015] URL: http://www.wikipedia.org/wiki/Median_Lethal_Dose.
Naylor, M.F. et al. Sun damage and prevention. (Apr. 24, 1996) [Online] URL: http://www.telemedicine.org/sundam2.4.1.html. [Retreived on May 8, 2013].
Newman M. D. et al. The safety of nanosized particles in titanium dioxide-and zinc oxide-based sunscreens. J Am Acad of Dermatol 61(4): 685-692 (Oct. 2009).
Ohtsu, H. et al. Antitumor agents. Part 217: Curcumin analogues as novel androgen receptor antagonists with potential as anti-prostate cancer agents. J med chem 45: 5037-5042 (2002).
Padhye, S. et al. Perspectives on chemopreventive and therapeutic potential of curcumin analogs in medicinal chemistry. Mini rev med chem 10(5): 372-387 May 2010.
Park, B. S. et al. Curcuma longa l. constituents inhibit sortase A and *Staphylococcus aureus* cell adhesion to fibronectin. J agric food chem 53(23): 9005-9009 (2005).
Phan, T. T. et al. Protective effects of curcumin against oxidative damage on skin cells in witro: it's implication for wound healing. J Trauma 51(5): 927-931 (Nov. 2001).
PL Detail-Document. New requirements for OTC sunsreen products. Pharmacist's Letter/Prescriber's Letter 6 pages (Aug. 2011).
Sharma, S. et al. Effect of insulin and its combination with resveratrol or curcumin in attenuation of diabetic neuropathic pain: participation of nitric oxide and tnf-alpha. Phytotherapy research 21(3): 278-283 (Mar. 2007).
Stankovic, I. Curcumin, chemical and technical assessment (cta) [online] [retrieved on May 13, 2013] URL: http://www.fao.org/fileadmin/templates/agns/pdf/jecfa/cta/61/Curcumin.pdf.
Suen, et al. Extraction of active constituents from turmeric and preparation of it's oil-based pigments. Science and Technology of Food Industry 24(7): 49-51 (2003).
Syu, W.J. et al. Cytotoxicity of curcuminoids and some novel compounds from curcuma zedoaria. J Nat Prod 61(12): 1531-1534 (Dec. 1998).
Tomren, M.A. et al. Studies on curcumin and curcuminoids xxxi. Symmetric and asymmetric curcuminoids: stability, activity and complexation with cyclodextrin. International Journal of Pharmaceutics 338(1-2): 27-34 (Jun. 29, 2007).
Tayyem, R.F. et al. Curcumin content of turmeric and curry powders. Nutrition and cancer 55(2): 126-131(2006).
Velasco, M.V. et al. Broad spectrum bioactive sunscreens. International journal of pharmaceutics 363(1-2): 50-57 (Nov. 3, 2008).
Wang, A. et al. Extraction of Turmeric Yellow Pigment and It's Stability Research. Shaanxi Chemical Industry 29(2):18-19 (2000).
Wang, Y. J. et al. Stability of curcumin in buffer solutions and characterization of its degradation products. Journal of pharmaceutical and biomedical analysis (15) 1867-1876 (1997).
Xie, X. et al. PLGA nanoparticles improve the oral bioavailability of curcumin in rats: characterizations and mechanisms. J Agric Food Chem 9280-9289 (Aug. 8, 2011).
Xu Jianguang, et al. Extraction, Separation of Curcumin Compounds and Performance Study. Chinese Master's Theses Full-text Database No. 4 (2012).
Yallapu M.M. et al. Fabrication of curcumin encapsulated plga nanoparticles for improved therapeutic effects in metastatic cancer cells. J Colloid Interface Sci 351(1): 19-29 (Nov. 1, 2010).

EDIBLE, SINGLE-EXTRACTION CURCUMA EXTRACTS

CROSS-REFERENCE TO RELATED APPLICATIONS

This application is a continuation of U.S. application Ser. No. 16/264,301, filed Jan. 31, 2019, which is a continuation of U.S. application Ser. No. 13/717,677, filed Dec. 17, 2012, now U.S. Pat. No. 10,231,940, which is a continuation of U.S. application Ser. No. 13/590,188, filed Aug. 21, 2012, each of which is hereby incorporated herein by reference in its entirety.

BACKGROUND

Field of the Invention

The teachings provided herein generally relate to formulations and uses of extracts of *Curcuma longa* L. plants for safe use topically, orally, rectally, or vaginally, for example.

Description of Related Art

A New Use of *Curcuma longa* L. Extract as a Sunscreen

The teachings provided herein shows that the *Curcuma longa* L. extract, surprisingly, has very good ultraviolet energy absorption properties across the entire wavelength range of interest, making it very attractive as a sunscreen agent. Moreover, the constituents of *Curcuma longa* L. have been shown to provide other therapeutic benefits. For example, antioxidant and anti-inflammatory effects have been shown, and treatments for Alzheimer's disease, Parkinson's disease, cystic fibrosis, liver injury, alcohol-induced liver disease, multiple sclerosis, human immunodeficiency virus (HIV), and cancer have been proposed. As such, the use of *Curcuma longa* L. extract as a sunscreen agent has the potential of providing additional therapeutic benefits that could far exceed merely protecting the skin from the UV rays of the sun.

There are clearly many sunscreen products on the market, and all utilize chemical agents to absorb UV radiation. UV radiation is the radiation that has shorter wavelengths than visible light and ranges from about 10 nm to 400 nm. The lower wavelengths, up to about 290 nm, are screened out by the earth's ozone layer and are generally of less interest. As such, sunscreen products focus on wavelengths ranging from 290 nm to 400 nm. Wavelengths ranging from 290 nm to 320 nm are considered "UVB" rays, and although UVB rays have a higher intensity, they also have less penetration power. As such, UVB rays may damage the superficial layers of skin but do not penetrate deeper, they do not penetrate glass, and their effects can generally be felt greatest between the hours of 10a and 4p in the US. Wavelengths ranging from 320 nm to 400 nm are considered "UVA" rays. UVA is less intense but penetrates deeper into the skin to cause damage to the deeper layers, through glass, and its effects are not limited to certain hours of the day. UVA has been considered to be less damaging than UVB due to it's lower intensity, and because UVB light has been identified as primarily responsible for sunburn, as well as melanoma and other skin cancers. However, UVA/s ability to cause damage at deeper layers of the skin, and because it's about 30 to 50 times more prevalent than UVB, much attention has recently been focused on UVA radiation. It has been shown, for example, that UVA can potentiate carcinogenesis from UVB and affects immune function. Interestingly, on Jun. 17, 2011, the FDA reported that sunscreen products should have both UVA and UVB protection, and that the UVA range has two unique areas of interest, the $UVA_1$ area ranging from 340 nm to 400 nm and the $UVA_2$ area ranging from 320 nm to 340 nm. The FDA stated that too much emphasis has been placed on UVB, that at least 20% of the protection should be in the $UVA_2$ region, and at least 60% of the protection should be in the $UVA_1$ region, stressing that the $UVA_1$ region is important.

A problem is that currently available sunscreen chemicals absorb light in either the UVA or UVB range. As such, the desired level of protection for the consumer, as indicated by at least the FDA, is not readily available. Currently, to address this problem, the art uses (i) titanium dioxide to extend the UVA range of protection, (ii) a combination of sunscreen agents to overlap and broaden the spectrum of UV protection, or (iii) a combination of titanium dioxide and overlapping ranges. Significant problems still remain, however. One problem is that the overlapping of peaks leaves skin exposed to weak protection in areas of the UV spectrum due to an inability to adequately overlap protection across the UV spectrum. Another problem is that the titanium dioxide can penetrate the skin, and this makes it particularly problematic in that it can potentially convert to compounds that pose a cancer risk when exposed to the UV energy.

The Problems of Producing a *Curcuma longa* L. Extract

Extraction methods that currently exist suffer several problems. One problem is that these methods incorporate undesirable chemicals at undesirable levels, for example, ethylene dichloride, methylene dichloride, and ethyl acetate. Ethanol can also be used, but it can only be present to a limited extent for internal consumption, and topical application is also limited due to side effects. As such, much effort has been spent trying to keep residual solvents below limits. Current extraction processes, for example, generally require complex processes that include removal of undesirable or toxic extraction solvents to meet FDA rules, and this can include, for example, distillation of the solvent to form a powder of the extract, a back-extraction of the extract into a different solvent that is suitable for a particular use, complexing with metal ions, use of high pH to precipitate a complex with ammonia, washing with methanol and water, and drying at high temperatures. In view of at least the above, current extraction methods suffer from (i) use of toxic solvents that require steps to remove and risk the presence of toxic residuals; (ii) heating in multiple steps to extract and purify; (iii) use of a high pH up to 9.5 on *Curcuma longa* L., which degrades above pH 7.0; and, ipso facto (iv) multi-step processes that are complex and expensive. There is currently no extraction process for *Curcuma longa* L. that uses a solvent that is suitable for both topical use and internal consumption.

Improving the Use of *Curcuma longa* L. Extract in Other Administrations, Such as Oral or Rectal Administrations Herbal preparations, including *Curcuma* root, are offered commercially, usually as capsules containing the dried and ground plant material. *Curcuma longa* L. can be used as an antioxidant, as a free radical scavenger, to remove reactive oxygen species (ROS) implicated in many diseases, making these species unavailable to human tissues. It can also be used as an antiflammatory. A problem is that the current preparations are typically large in order to obtain a desired dosage, or multiple capsules have to be taken, resulting in an inconvenience to the consumer and, of course, non-compliance. Stable, concentrated formulations, such as solutions, emulsions, microemulsions, and nanoemulsions, would be appreciated by those skilled in the art in order to increase compliance of administration, as well as the bioavailability, of the components of the extract after administration.

One of skill in the art will appreciate having (i) a sunscreen with a very broad band of absorption with desired strength across the UVA and UVB ranges without requiring the addition of titanium dioxide. In addition, the art would appreciate having (ii) a process of producing the extract without requiring the removal of the extraction solvent, reducing complexity and cost of processing. Moreover, the art would also appreciate (iii) an antioxidant dosage form that not only can be used directly from the extraction process, but also is potent and concentrated to a smaller quantity for consumption for increased compliance with a variety of administrations and uses. In particular, the art would appreciate having (iv) microemulsion and nanoemulsion formulations that can be easily produced directly from the extraction process without requiring further separation of extraction solvents, the emulsions providing an enhancement to the bioavailability of the extracts as well as an increased stability. And, the art would also appreciate having (v) extract formulations that can be used in combination as a topically, orally, and/or rectally administered composition for the variety of indications taught herein. Finally, the art will appreciate having extraction methods that can provide all of the above while also providing (vi) an extraction process having a significantly higher yield than state-of-the-art processes.

SUMMARY

The teachings provided herein generally relate to active compositions that can be isolated from plants in the Zingiberaceae family for safe use topically, orally, rectally or vaginally, for example, namely the *Curcuma* family, and more particularly *Curcuma longa* L. or "turmeric". In some embodiments, the teachings are directed to a composition for use as a sunscreen, the composition comprising an extract of a *Curcuma longa* L. root.

In some embodiments, the teachings are directed to a pharmaceutically acceptable composition comprising a purified liquid extract from the roots of a *Curcuma longa* L. plant. The liquid extract can comprise compounds of interest, such as curcumin; demethoxycurcumin; bisdemethoxycurcumin; or, a combination thereof. The liquid extract also contains an at least substantially non-toxic extraction solvent that removes the compounds of interest from the roots of a *Curcuma longa* L. plant in an extraction process; and, functions as a pharmaceutically acceptable carrier having (i) an acute oral toxicity with an LD50 of at least 49,700 mg/kg or (ii) an acute dermal toxicity of at least 5000 mg/kg; wherein, the extraction solvent was used in the extraction process that removed the extract from the roots of the *Curcuma longa* L. plant and chosen to remain as a component of the pharmaceutically acceptable composition.

It should be appreciated that the term "purified" can be used to refer to an extract from a *Curcuma longa* plant, in some embodiments, such that the compounds of interest are isolated from the remainder of the plant in a soluble form. As such, one of skill will appreciate that the compounds of interest can sometimes be accompanied by other components of the plant that are carried along with the extract. For example, such other components can include those selected from the group consisting of hemicellulose, resins, oils, volatiles, inorganic salts, or any combination thereof. In some embodiments, the term "purified" can be used to refer to an extract consisting of, or consisting essentially of, any one or any combination of the compounds of interest. In some embodiments, the extract includes the extraction solvent. In some embodiments, an extract "consists essentially of" any one or any combination of the compounds of interest, where the presence of any other component from the plant has a negligible effect on the activity of the compounds of interest. The term "negligible effect" can be used to mean that the activity does not increase or decrease more than about 10% when compared to any one or any combination of the compounds of interest, respectively, without the other components. In some embodiments, the term "negligible effect" can be used to refer to a change of less that 10%, less than 9%, less than 8%, less than 7%, less than 6%, less than 5%, less than 4%, and less than 3%. In some embodiments, the term "negligible effect" can be used to refer to a change ranging from about 3% to about 10%, in increments of 1%. In some embodiments, the other components, for example, the hemicellulose, resins, oils, volatiles, inorganic salts, or any combination thereof, can enhance the activity of the compounds of interest. For example, the activity of the compounds of interest can be enhanced by an amount ranging from about 10% to about 300%, from about 20% to about 200%, from about 25% to about 250%, from about 30% to about 300%, from about 35% to about 275%, from about 40% to about 225%, from about 15% to about 100%, or any range therein in increments of 1%.

It should be appreciated that the term "extract" can be used to refer to a powder form of the compounds of interest, a liquid form of the compounds of interest, or any one or any combination of the compounds of interest in powder or liquid form. One of skill will appreciate that the term "extract" can be used to refer to the compounds of interest before, during, or after their removal from the plant. In some embodiments, the compounds of interest can be synthesized chemically using standard methods known to one of skill, such that they can be synthesized and used alone, or in any combination, by those of skill without use of the extraction methods taught herein.

Any dosage form known to one of skill can be used for administrations that include, for example, topical, oral, rectal, or vaginal administration. In some embodiments, the composition is in a dosage form for administration topically for any use set-forth herein. In some embodiments, the composition is applied topically as a sunscreen. And, in some embodiments, the composition is in a dosage form for administration orally. In some embodiments, the dosage form can be a capsule or tablet. The composition can be used as a dietary supplement. In some embodiments, the dietary supplement can function as an antioxidant in a subject.

The teachings are also directed to a pharmaceutically acceptable emulsion comprising a purified liquid extract from the roots of a *Curcuma longa* L. plant. The emulsion can comprise curcumin; demethoxycurcumin; bisdemethoxycurcumin; or, a combination thereof. The emulsion includes an at least substantially non-toxic extraction solvent that removes the extract from the roots of a *Curcuma longa* L. plant in an extraction process; and, functions as a pharmaceutically acceptable carrier having (i) an acute oral toxicity with an LD50 of at least 49,700 mg/kg or (ii) an acute dermal toxicity of at least 5000 mg/kg; wherein, the extraction solvent was (iii) used in the extraction process that remove the extract from the roots of the *Curcuma longa* L. plant and (iv) chosen to remain as a component of the pharmaceutically acceptable composition. The emulsion comprises a pharmaceutically acceptable oil; and, an emulgent. One of skill will appreciate that an emulsion can be considered as a fine dispersion of minute droplets of one liquid in another in which it is not soluble or miscible. As such, an emulsion containing a pharmaceutically acceptable oil and an emulgent can also contain water, an alcohol, or any other suitable hydrophilic liquid such as, for example, polyethylene glycol 200 (PEG200) or polyethylene glycol 400 (PEG 400).

The teachings are also directed to methods of preparing the pharmaceutically acceptable compositions taught herein. The methods can comprise macerating at least a portion of a *Curcuma longa* L. root for an effective time in the at least substantially non-toxic extraction solvent. In these embodiments, the extraction solvent is miscible with phenolic diketones that include curcumin, demethoxycurcumin, and bisdemethoxycurcumin; and, pharmaceutically acceptable as a carrier for the phenolic diketones. As a carrier, it should have (i) an acute oral toxicity with an LD50 of at least 49,700 mg/kg or (ii) an acute dermal toxicity of at least 5000 mg/kg. The macerating includes covering the portion of the root with the extraction solvent. The method also includes separating the extraction solvent from the macerated root to create a liquid extract of *Curcuma longa* L.

The teachings are also directed to a method of preparing the pharmaceutically acceptable emulsions that include the extracts taught herein. The method comprises macerating at least a portion of a *Curcuma longa* L. root for an effective time in the at least substantially non-toxic extraction solvent that is miscible with phenolic diketones that include curcumin, demethoxycurcumin, and bisdemethoxycurcumin; and pharmaceutically acceptable as a carrier for the phenolic diketones, the carrier having (i) an acute oral toxicity with an LD50 of at least 49,700 mg/kg or (ii) an acute dermal toxicity of at least 5000 mg/kg. The method also includes separating the extraction solvent from the macerated root to create a liquid extract of *Curcuma longa* L. and, emulsifying the liquid extract.

In some embodiments, the emulsifying includes adding a pharmaceutically acceptable oil to the liquid extract to create the emulsion of the liquid extract. And, in some embodiments, the emulsifying includes adding an emulgent to the liquid extract to create the emulsion of the liquid extract as described above.

The extraction solvents used in the teachings can be any such extraction solvent, or any combination of such solvents, known to one of skill that meets the criteria. In some embodiments, the extraction solvent comprises polyoxyethylene (20) sorbitan monooleate (TWEEN 80), polyethylene glycol, isopropyl myristate, or a combination thereof. In some embodiments, the extraction solvent comprises a combination of TWEEN 80 and isopropyl myristate. In some embodiments, the extraction solvent comprises a ratio of TWEEN 80:isopropyl myristate ranging from about 20:80 to about 50:50.

The pharmaceutically acceptable oil used in the teachings can be any such oil, or any combination of oils, known to one of skill that meets the criteria. In some embodiments, the pharmaceutically acceptable oil comprises an oil selected from the group consisting of an animal oil, a fish oil, a vegetable oil, or a mineral oil. In some embodiments, the pharmaceutically acceptable oil comprises an edible oil selected from the group consisting of olive oil, sunflower oil, sesame oil, almond oil, corn oil, orange oil, lime oil, black pepper oil, nutmeg oil, basil oil, rosemary oil, clove oil, grapefruit oil, fennel oil, coriander oil, bergamot oil, cinnamon oil, lemon oil, peppermint oil, garlic oil, thyme oil, marjoram oil, lemongrass oil, ginger oil, cardamon oil, liquid paraffin, cotton seed oil, peanut oil, nut oil, soy oil, rapeseed oil, vitamin E oil, Vitamin E TPGS oil, fish oil, tallow-derived oil, silicone oil, castor oil, squalene oil, or any mixture thereof.

The teachings are also directed to kits that contain a combination of topical, oral, or rectal dosage forms for administrations to a subject. In some embodiments, the kit is for protecting a dermal tissue from UVA and UVB exposure, the kit comprising an extract of a *Curcuma longa* L. root in an oral dosage form; an extract of a *Curcuma longa* L. root in a topical dosage form; and, instructions for administration of the topical dosage form, the oral dosage form, or a combination of the topical and oral dosage forms.

The extracts taught herein can be used for a variety of treatments. In some embodiments, the teachings are directed to a method of treating a skin to prevent or inhibit exposure of the skin to UVA and UVB, the method comprising topically administering an effective amount of a composition taught herein to a dermal tissue of a subject. In some embodiments, the methods further comprise orally administering an effective amount of an oral dosage form of a composition taught herein to a subject to systemically treat a disease or disorder, such as a disease or disorder taught herein. In some embodiments, the methods further comprise orally administering an effective amount of an oral dosage form of a composition taught herein to a subject as a dietary supplement. In some embodiments, the methods further comprise orally administering an effective amount of an oral dosage form of a composition taught herein to a subject in combination with the topical administration.

In some embodiments, the teachings are directed to a method of treating an inflammation of a tissue of subject, the method comprising administering an effective amount of a composition taught herein to a tissue of the subject. In some embodiments, the teachings are directed to treating a wounded tissue, the method comprising administering an effective amount of a composition taught herein to a tissue of the subject.

Any tissue that can make contact with one or more active components of an extract taught herein can be treated. The tissue can be, for example, connective, muscle, nervous, and/or epithelial tissue. In some embodiments, the tissue is a dermal tissue. In some embodiments, the tissue is a mucosal tissue. And, in some embodiments, the tissue is gastrointestinal tissue. In some embodiments, a first tissue makes contact with one or more active components of an extract taught herein and a second tissue realizes a benefit as a secondary effect.

One of skill reading the teachings that follow will appreciate that the concepts can extend into additional embodiments that go well-beyond a literal reading of the claims, the inventions recited by the claims, and the terms recited in the claims.

DETAILED DESCRIPTION

Figure 1A:
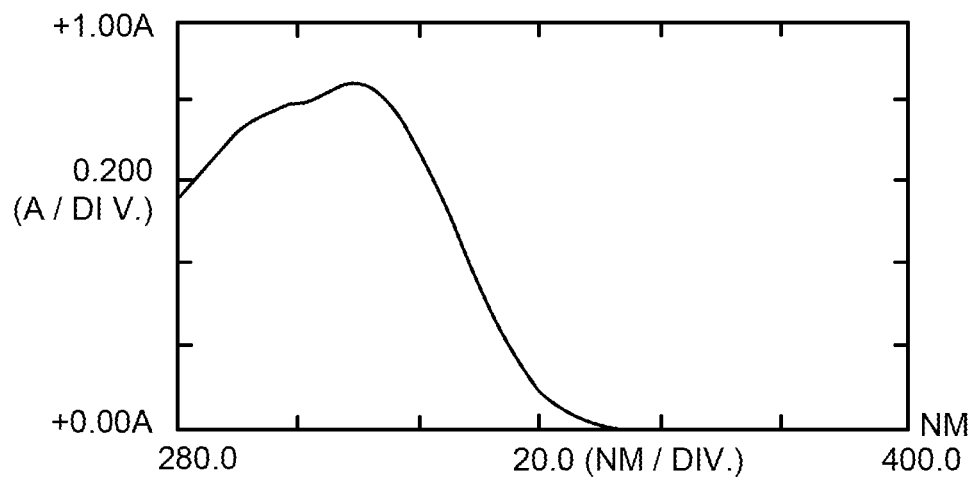
FIGS. 1A-1F compare the absorption spectra of representative current state-of-the-art sunscreen agents to the absorption spectra of *Curcuma longa* L., according to some embodiments.

The teachings provided herein generally relate to active extracts, compositions that can be isolated from plants in the Zingiberaceae family for use topically, orally, rectally, or vaginally, for example, namely the *Curcuma* genus, and more particularly *Curcuma longa* L. or "turmeric". Any active extract obtained from the Zingiberaceae family can be used in aspects of the teachings herein. In some embodiments, the teachings are directed to a composition for use as a sunscreen, the composition comprising an extract of a *Curcuma longa* L. root.

In some embodiments, an extract from the *Curcuma*, or *Curcuma* L., genus can be used. In some embodiments, the extract can be from *Curcuma aeruginosa, Curcuma albicoma, Curcuma albiflora, Curcuma alismatifolia, Curcuma amada* Roxb, *Curcuma amarissima, Curcuma angustifolia, Curcuma aromatica, Curcuma attenuata, Curcuma aurantiaca, Curcuma australasica, Curcuma bakeriana, Curcuma bicolor, Curcuma bhatii, Curcuma burttii, Curcuma caesia, Curcuma ceratotheca, Curcuma chuanezhu, Curcuma chuanhuangjiang, Curcuma chuanyujin, Curcuma cochinchinensis, Curcuma codonantha, Curcuma coerulea, Curcuma colorata, Curcuma comosa, Curcuma coriacea, Curcuma decipiens, Curcuma domestica, Curcuma ecalcarata, Curcuma euchroma, Curcuma ecomata, Curcuma elata, Curcuma exigua, Curcuma ferruginea, Curcuma flaviflora, Curcuma glans, Curcuma gracillima, Curcuma grandiflora, Curcuma haritha, Curcuma harmandii, Curcuma heyneana, Curcuma inodora, Curcuma inodora, Curcuma karnatakensis, Curcuma kudagensis* Velayudhan, *Curcuma kwangsiensis, Curcuma lanceolata, Curcuma larsenii, Curcuma latiflora, Curcuma latifolia, Curcuma leucorrhiza, Curcuma loerzingii, Curcuma longa* L, *Curcuma longa, Curcuma longispica, Curcuma malabarica, Curcuma meraukensis, Curcuma mutabilis, Curcuma neilgherrensis, Curcuma nilamburensis, Curcuma oligantha, Curcuma ornata, Curcuma parviflora, Curcuma parvula, Curcuma peethapushpa, Curcuma petiolata, Curcuma phaeocaulis, Curcuma pierreana, Curcuma plicata, Curcuma porphyrotaenia, Curcuma prakasha, Curcuma pseudomontana, Curcuma purpurascens, Curcuma purpurea, Curcuma raktakanta, Curcuma reclinata, Curcuma rhabdota, Curcuma rhomba, Curcuma roscoeana, Curcuma rubescens, Curcuma rubrobracteata, Curcuma sattayasaii, Curcuma sichuanensis, Curcuma singularis, Curcuma sparganiifolia, Curcuma stenochila, Curcuma strobilifera, Curcuma sulcata, Curcuma sumatrana, Curcuma sylvatica, Curcuma thalakaveriensis, Curcuma thorelii, Curcuma trichosantha, Curcuma vamana, Curcuma vellanikkarensis, Curcuma wenyujin, Curcuma wenchowensis, Curcuma xanthorrhiza, Curcuma yunnanensis, Curcuma zedoaria, Curcuma zedoaroides,* and any combination thereof.

In some embodiments, the extract can be from *Curcuma aeruginosa, Curcuma domestica, Curcuma longa, Curcuma manga, Curcuma xanthorriza,* or a combination thereof. In some embodiments, the extract can be from *Alpina galaiga, Amonum kepulaga, Phoeomera speciosa, Zinger cassumunar,* or a combination thereof.

The compositions provided herein can be referred to as extracts, compositions, compounds, agents, active agents, bioactive agents, supplements, drugs, and the like. In some embodiments, the terms "composition," "compound," "agent," "active", "active agent", "bioactive agent," "supplement," and "drug" can be used interchangeably and, it should be appreciated that, a "formulation" can comprise any one or any combination of these. Likewise, in some embodiments, the composition can also be in a liquid or dry form, where a dry form can be a powder form in some embodiments, and a liquid form can include an aqueous or non-aqueous component. Moreover, the term "bioactivity" can refer to the function of the compound when administered orally, topically, or rectally to a subject.

In some embodiments, the term "target site" can be used to refer to a select location on or in a subject that could benefit from an administration of a compound taught herein, either topically or orally. In some embodiments, a target can include any site of action in which the agent's activity, such as antioxidant activity, anti-inflammatory activity, or UVA and UVB blocking activity, can serve a benefit to the subject. The target site can be a healthy or damaged tissue of a subject. As such, the teachings include a method of administering one or more compounds taught herein to a healthy or damaged tissue, dermal, mucosal, gastrointestinal or otherwise.

One of skill will appreciate that the compositions or formulations should remain stable, or at least substantially stable, until useful or activated, and this can relate to a shelf life, or a time between creation and administration of the composition, or some combination thereof. In some embodiments, the composition is stable, or substantially stable, when usable as intended within a reasonable amount of time, a time that is considered reasonable by one of skill for the applications taught herein. In some embodiments, the composition should be usable within a reasonable time from the making to the administration of the composition and, in some embodiments, the composition should have a reasonable commercial shelf life, a shelf life that is considered reasonable to one of skill. A reasonable shelf life can be at least 6 months, at least 1 year, at least 18 months, at least 2 years, at least 3 years, or any time in-between in increments of about 1 month, in some embodiments.

In some embodiments, a composition or formulation can be considered as "stable" if it loses less than 10% of its original activity. In some embodiments, a composition or formulation can be considered as stable if it loses less than 5%, 3%, 2%, or 1% of its original activity. In some embodiments, a composition or formulation can be considered as "substantially stable" if it loses greater than about 10% of its original activity, as long as the composition can perform it's intended use to a reasonable degree of efficacy. In some embodiments, the composition can be considered as substantially stable if it loses activity at an amount greater than about 12%, about 15%, about 25%, about 35%, about 45%, about 50%, about 60%, or even about 70%. The activity loss can be measured by comparing activity at the time of packaging to the activity at the time of administration, and this can include a reasonable shelf life. In some embodiments, the composition is stable or substantially stable, if it remains useful for a period ranging from 3 months to 3 years, 6 months to 2 years, 1 year, or any time period therein in increments of about 1 month.

Methods of Use

The extracts taught herein can be used for a variety of treatments, preventative, ameliorative, or otherwise, as well as for use as a dietary supplement. The uses can include medicinal purposes, as a health supplement, a nutritional composition, a prophylactic, or a treatment of an existing condition. In some embodiments, any tissue that can make contact with one or more active components of an extract taught herein can be treated. In some embodiments, a tissue can have a desirable secondary effect from one or more of the active components of an extract taught herein making contact elsewhere in the subject, such that one or more of the active components can contact a first tissue, whereas a second tissue realizes a beneficial effect. For example, the first tissue can be a stomach lining, and the second tissue can realize the desirable effect of a release of a neurotransmitter or a neuroimpulse. The tissue can be, for example, connective, muscle, nervous, and/or epithelial tissue. In some embodiments, the tissue is a dermal tissue. In some embodiments, the tissue is a mucosal tissue. And, in some embodiments, the tissue is gastrointestinal tissue.

The terms "treat," "treating," and "treatment" can be used interchangeably in some embodiments and refer to the administering or application of the compositions and formulations taught herein, including such administration as a health or nutritional supplement, and all administrations directed to the prevention, inhibition, amelioration of the symptoms, or even a cure of a condition taught herein. The terms "disease," "condition," "disorder," and "ailment" can be used interchangeably in some embodiments. The term "subject" and "patient" can be used interchangeably in some embodiments and refer to an animal such as a mammal including, but not limited to, non-primates such as, for example, a cow, pig, horse, cat, dog, rat and mouse; and primates such as, for example, a monkey or a human. As such, the terms "subject" and "patient" can also be applied to non-human biologic applications including, but not limited to, veterinary, companion animals, commercial livestock, and the like.

In some embodiments, the teachings are directed to a method of treating a skin to prevent or inhibit exposure of the skin to UVA and UVB, the method comprising topically administering an effective amount of a composition taught herein to a dermal tissue of a subject. In some embodiments, the methods further comprise orally administering an effective amount of an oral dosage form of a composition taught herein to a subject to systemically treat a disease or disorder, such as a disease or disorder taught herein. In some embodiments, the methods further comprise orally administering an effective amount of an oral dosage form of a composition taught herein to a subject as a dietary supplement. In some embodiments, the methods further comprise orally administering an effective amount of an oral dosage form of a composition taught herein to a subject in combination with the topical administration. In some embodiments, the teachings are directed to a method of treating an inflammation of a tissue of subject, the method comprising administering an effective amount of a composition taught herein to a tissue of the subject. In some embodiments, the teachings are directed to treating a wounded tissue, the method comprising administering an effective amount of a composition taught herein to a tissue of the subject.

An "effective amount" of a compound can be used to describe a therapeutically effective amount or a prophylactically effective amount. An effective amount can also be an amount that ameliorates the symptoms of a disease. A "therapeutically effective amount" can refer to an amount that is effective at the dosages and periods of time necessary to achieve a desired therapeutic result and may also refer to an amount of active compound, prodrug or pharmaceutical agent that elicits any biological or medicinal response in a tissue, system, or subject that is sought by a researcher, veterinarian, medical doctor or other clinician that may be part of a treatment plan leading to a desired effect. In some embodiments, the therapeutically effective amount should be administered in an amount sufficient to result in amelioration of one or more symptoms of a disorder, prevention of the advancement of a disorder, or regression of a disorder. In some embodiments, for example, a therapeutically effective amount can refer to the amount of an agent that provides a measurable response of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of a desired action of the composition.

In cases of the prevention or inhibition of the onset of a disease or disorder, or where an administration is considered prophylactic, a prophylactically effective amount of a composition or formulation taught herein can be used. A "prophylactically effective amount" can refer to an amount that is effective at the dosages and periods of time necessary to achieve a desired prophylactic result, such as prevent the onset of a sunburn, an inflammation, allergy, nausea, diarrhea, infection, and the like. Typically, a prophylactic dose is used in a subject prior to the onset of a disease, or at an early stage of the onset of a disease, to prevent or inhibit onset of the disease or symptoms of the disease. A prophylactically effective amount may be less than, greater than, or equal to a therapeutically effective amount.

In some embodiments, a therapeutically or prophylactically effective amount of a composition may range in concentration from about 0.01 nM to about 0.10 M; from about 0.01 nM to about 0.5 M; from about 0.1 nM to about 150 nM; from about 0.1 nM to about 500 µM; from about 0.1 nM to about 1000 nM, 0.001 µM to about 0.10 M; from about 0.001 µM to about 0.5 M; from about 0.01 µM to about 150 µM; from about 0.01 µM to about 500 µM; from about 0.01 µM to about 1000 nM, or any range therein. In some embodiments, the compositions may be administered in an amount ranging from about 0.005 mg/kg to about 100 mg/kg; from about 0.005 mg/kg to about 400 mg/kg; from about 0.01 mg/kg to about 300 mg/kg; from about 0.01 mg/kg to about 250 mg/kg; from about 0.1 mg/kg to about 200 mg/kg; from about 0.2 mg/kg to about 150 mg/kg; from about 0.4 mg/kg to about 120 mg/kg; from about 0.15 mg/kg to about 100 mg/kg, from about 0.15 mg/kg to about 50 mg/kg, from about 0.5 mg/kg to about 10 mg/kg, or any range therein, wherein a human subject is often assumed to average about 70 kg. In addition to use as a sunscreen as provided herein, the extracts taught herein can provide a number of therapeutic benefits. Such benefits can include, for example, free radical scavenger and antioxidant, inhibiting lipid peroxidation and oxidative DNA damage; anti-inflammatory activity; neurological treatments for Alzheimer's disease (anti-amyloid and other effects), Parkinson's disease, and other neurological disorders; anti-arthritic treatment; anti-ischemic treatment; treatments for multiple myeloma and myelodysplastic syndromes; psoriasis treatments (topically and orally); cystic fibrosis treatments; treatments for liver injury and alcohol-induced liver disease; multiple sclerosis treatments; antiviral treatments, including human immunodeficiency virus (HIV) therapy; treatments of diabetes; cancer treatments; and, reducing risk of heart disease; to name a few.

As such, the use of *Curcuma longa* L. extract as a sunscreen agent has the potential of providing additional therapeutic benefits that could far exceed merely protecting the skin from UV the rays of the sun. On the skin, this effect may aid in preventing reactions in individuals with sensitive skin. The limitation of these reactions may help in flushing, blushing, rosacea and similar disorders in such individuals. Given the above, the application of the sunscreen may provide beneficial effects to sportsmen who apply it since minor scratches and injuries sustained during a sports game may heal faster. It would have a similar advantage to gardeners, those at the beach, hikers and so on. The extracts can be used, for example, as a dietary supplement or a pharmaceutically acceptable dosage form.

In some embodiments, the extracts taught herein can be used as an antioxidant by the oral route, as a free radical scavenger, to remove reactive oxygen species (ROS) implicated in many diseases, making these species unavailable to human tissues. In some embodiments, the dietary supplement can function as an antioxidant in a subject. The composition can be used as a dietary supplement in some embodiments.

The compositions or formulations are also useful in treating inflammations. In some embodiments, they can be administered for treating inflammations of any tissue such as, for example, skin, mucosal, or gastrointestinal inflammations in a subject, in which they can be administered, for example, topically, orally, rectally, or vaginally to prevent, treat, inhibit, or ameliorate the symptoms of an inflammation of the tissue.

In some embodiments, the compositions and formulations can be used to prevent, treat, ameliorate the symptoms of, or even cure, an acute or chronic gastrointestinal condition. Such conditions can include, but are not limited to, hyperacidity, colitis, irritable bowel syndrome, Crohn's disease, necrotic enteritis, functional colonic diseases, malabsorption, a peptic ulcer, gastro-esophageal reflux disease, ulcerative colitis, and diverticulitis. In some embodiments, the compositions and formulations can be used to reduce mucosal tissue inflammation, dysfunction, or damage. Such conditions can be induced, for example, by drug side effects, chemotherapy, dysbiosis, radiation, changes in normal flora, hyperimmunity, autoimmune reactions, immune deficiencies, nervousness, allergies, chemical irritation, and stress. In some embodiments, the symptoms of a gastrointestinal condition can include, for example, diarrhea, dehydration, malnutrition, constipation, nausea, and/or cramping. And, in some embodiments, the symptoms of a gastrointestinal condition can be temporary and include acid irritation, indigestion, bloating, cramps, spasmodic peristalsis, diarrhea, and constipation. Administering the compositions or formulations for the treatment and/or management of gastrointestinal conditions can be considered a nutritional or health supplement, in some embodiments.

The compositions or formulations are also useful in treating wounds. Generally speaking, they can be administered to protect, promote healing, or improve function of skin or mucosa. In some embodiments, for example, a wound and a chronic inflammatory condition can be treated including, but not limit to, a wound by (i) physical damage, (ii) a diabetic skin lesion, (iii) a bed sore, (iv) a burn, (v) a cold sore, (vi) psoriasis, (vii) eczema, and (viii) dermatological inflammation caused by pathogens, to name a few.

Making and Administering the Extract

Making the *Curcuma longa* Extract

Generally speaking, at least a portion of a root of *Curcuma longa* L., for example, can be crushed and then soaked in a solvent to create a macerate. The macerate can be filtered and the residue can be re-extracted multiple times. The extract can be adjusted for potency and stored in amber bottles. The extract may be prepared as an alcoholic extract, an oily extract or another type of organic solvent may be used. The extract may be used as an alcoholic solution or the solvent may be evaporated and the dry powder incorporated into suitable formulations for human use. The extraction may also be done using oils suitable for human use as the solvent with the advantage of incorporating the extract directly into sunscreen cream or lotion formulations.

In some embodiments, the solvent can be a lower alkanol. The concentrations of lower alkanol used in the extractions can range from, for example, 20%-30%, 30%-40%, 40%-50%, 50%-60%, 60%-70%, 70%-80%, 80%-90%, or any concentration therein. The alkanol can be used in additional washes for further purification of the extract. An extract precipitate, for example, can be washed with more of the lower alkanol, where a typical wash may include, for example, three washes with 95% ethanol. The precipitate can then be suspended in water at a concentration suitable for further processing such as, for example, about 18-20% weight/volume. Re-precipitation by again adding a lower alkanol in the water can be used to remove additional materials that are not water-soluble. The supernatant can be precipitated with a higher concentration of the lower alkanol.

In some embodiments, the higher concentration of the lower alkanol can be, for example, ethanol. Ethanol appears to be a favorable extraction solvent, at least with regard to separating the extract from the plant, as a comparatively high yield is obtained when compared to other state-of-the-art methods. In addition, the extract is not viscous which makes filtration easier. Since ethanol is a suitable extraction solvent and oils can be incorporated into formulations, it is also possible to re-extract an ethanol extract into suitable oils, such as sesame seed oil. For the latter, several extraction steps may be necessary.

In some embodiments, 40-80% ethanol, 60-70% ethanol, or 50-60% ethanol can be used to create a crude extract. In some embodiments, the ethanol can be added at a concentration of about 70% ethanol at about room temperature, and the extraction can be done in steps by first using a lower concentration of about 35% ethanol in a first step, and then using a higher concentration of about 70% ethanol in a second step.

In some embodiments, the extract can be dried. The application of heat, however, should be carefully performed, as the extracts degrade when subject to heat and, thus, the activity of the extract can be deleteriously affected. In general, it is better to heat for the shortest time possible to limit degradation. In some embodiments, the extract can be dried for a time ranging from about 30 seconds to about 1 minute, from about 1 minute to about 5 minutes, from about 5 minute to about 10 minutes, from about 10 minute to about 20 minutes, from about 20 minute to about 30 minutes, from about 30 minute to about 40 minutes. In some embodiments, the extract can be dried for a time ranging for a time ranging from about 30 minutes to 1 hour or more, depending on the conditions used. In some embodiments, heat can be applied at temperatures below about 90° C., ranging from about 30° C. to about 80° C., from about 40° C. to about 70° C., from about 50° C. to about 60° C., from about 70° C. to about 80° C., or any range therein. In some embodiments, the heating can be at a temperature ranging from 25° C. to 70° C. in any increment of about 5° C. It should be appreciated that any process known to one of skill that avoids any heating, or at least excessive heating can be used, including, for example, drying in a dessicator at room temperature, spray drying, vacuum drying, freeze-drying, critical point drying, solvent exchange, and any combination thereof known to one of skill.

In some embodiments, the extract can be filtered. For example, an extract can be re-dissolved, and brought to a suitable concentration for filtration to further remove unwanted materials. In some embodiments, the suitable concentration for filtration can be about 1%, about 2%, about 3%, about 4%, about 5%, about 6%, about 7%, about 8%, about 9%, about 10%, about 12%, about 14% or any concentration therein in increments of 0.2%.

In some embodiments, the extraction is done using an oil or other solvent. In some embodiments, the solvent can include a surfactant. Example surfactants include anionic, cationic, zwitterionic, and nonionic surfactants. An example of cationic surfactants includes sodium dodecylsulfate (SDS). An example of anionic surfactants includes cetylpyridinium bromide. An example of zwitterionic surfactants includes dipalmitoylphosphatidylcholine (lecithin). An example of noninionic surfactants includes polyoxyethylene(4) lauryl ether (BRIJ 30). In some embodiments, SPAN- or TWEEN-type surfactants can be used, including SPAN 60, SPAN 80, TWEEN 60, and TWEEN 80. In fact, any one or any combination of the numerous surfactants known to one of skill can be used to the extent that there is reason to believe that such use would be consistent with the teachings provided herein.

In some embodiments, the solvent can include an oil. The oil and/or surfactant can be used to extract the root, *Curcuma longa* L., by crushing the root and soaking the crushed root in the solvent to form a macerate. The macerate is then filtered to leave an extract. The macerate will often contain more extract and, as such, the residue may be re-extracted multiple times in some embodiments, and any one or combination of solvents can be used to obtain the extract from the root. In some embodiments, sesame seed oil can be used, as it is considered at least substantially non-toxic and light, such that the extract can be filtered easily and not display excessive oiliness when applied to the skin.

Method of preparing the pharmaceutically acceptable compositions taught herein can comprise macerating at least a portion of a *Curcuma longa* L. root for an effective time in the at least substantially non-toxic extraction solvent. In these embodiments, the extraction solvent is miscible with phenolic diketones that include curcumin, demethoxycurcumin, and bisdemethoxycurcumin; and, pharmaceutically acceptable as a carrier for the phenolic diketones. The method also includes separating the extraction solvent from the macerated root to create a liquid extract of *Curcuma longa* L.

The teachings are also directed to a method of preparing the pharmaceutically acceptable emulsions that include the extracts taught herein. In some embodiments, the emulsifying includes adding a pharmaceutically acceptable oil to the liquid extract create the emulsion of the liquid extract. And, in some embodiments, the emulsifying includes adding an emulgent to the liquid extract create the emulsion of the liquid extract. As such, the method can comprise macerating at least a portion of a *Curcuma longa* L. root for an effective time in the at least substantially non-toxic extraction solvent that is miscible with phenolic diketones that include curcumin, demethoxycurcumin, and bisdemethoxycurcumin; and pharmaceutically acceptable as a carrier for the phenolic diketones. The method also includes separating the extraction solvent from the macerated root to create a liquid extract of *Curcuma longa* L. and, emulsifying the liquid extract.

The term "at least substantially non-toxic" can be used to mean that the extraction solvent is substantially less toxic than ethanol, such that one of skill would be able to use at least 50%, 75%, 100%, 200%, or 300% more of the solvent as compared to ethanol in a formulation for use as a topical, oral, or rectal formulation. The guidelines for use can follow the US FDA regulations. In some embodiments, the extraction solvent has (i) an acute oral toxicity with an LD50 of at least 49,700 mg/kg or (ii) an acute dermal toxicity of at least 5000 mg/kg.

The extraction solvents used in the teachings can be any such extraction solvent, or any combination of such solvents, known to one of skill that meets the criteria. In some embodiments, the extraction solvent comprises polyoxyethylene (20) sorbitan monooleate (TWEEN 80), polyethylene glycol, isopropyl myristate, or a combination thereof. In some embodiments, the extraction solvent comprises a combination of TWEEN 80 and isopropyl myristate. In some embodiments, the extraction solvent comprises a ratio of TWEEN 80:isopropyl myristate ranging from about 20:80 to about 50:50.

The pharmaceutically acceptable oil used in the teachings can be any such oil, or any combination of oils, known to one of skill that meets the criteria. In some embodiments, the pharmaceutically acceptable oil comprises an oil selected from the group consisting of an animal oil, a fish oil, a vegetable oil, or a mineral oil. In some embodiments, the pharmaceutically acceptable oil comprises an edible oil selected from the group consisting of olive oil, sunflower oil, sesame oil, almond oil, corn oil, orange oil, lime oil, black pepper oil, nutmeg oil, basil oil, rosemary oil, clove oil, grapefruit oil, fennel oil, coriander oil, bergamot oil, cinnamon oil, lemon oil, peppermint oil, garlic oil, thyme oil, marjoram oil, lemongrass oil, ginger oil, cardamon oil, liquid paraffin, cotton seed oil, peanut oil, nut oil, soy, rapeseed oil, vitamin E oil and derivatives thereof, including Vitamin E TPGS (d-alpha tocopheryl polyethylene glycol 1000 succinate), fish oil, tallow-derived oil, silicone oil, castor oil, squalene oil, or any mixture thereof.

Formulations

*Curcuma longa* L. can be applied to a target tissue non-parenterally. In some embodiments, the compositions or formulations can be applied at least topically, orally, rectally, or vaginally, for example. And, any suitable dosage form known to one of skill can be used for topical, oral, rectal, or vaginal administration.

The design of the formulations can include, for example, (i) identifying the condition or use; (ii) identifying the target site; and (ii) matching a dosage form for administration to the target site. Identifying the target site includes, for example, select a target tissue for treatment, such as a healthy or damaged tissue at which the formulation can be applied to prevent, inhibit, otherwise treat, or ameliorate the symptoms of a condition. Once the use, the target site, and the method of administration have been chosen, one of skill can readily select a dose, which will vary according to any of a variety of factors known the person of skill including, but not limited to, environmental conditions present at the site of use, for example, sunlight, heat, water, pH, gastric acids, and the like. In some embodiments, this formulation can be administered for uses in animals that are non-humans.

In some embodiments, the composition is in a dosage form for administration topically for any use set-forth herein. Topical administration can be used on any tissue that can benefit from a topical application, including the skin, mucous membranes, and gastrointestinal tract. For topical administration, suitable formulations may include a biocompatible oil, wax, gel, powder, emulsion, polymer, or other liquid or solid carriers. Such formulations may be administered by applying directly to affected tissues. For example, a cream formulation can be administered to a target area on the skin. Transdermal administrations are also possible, including percutaneous absorption of the *Curcuma* compounds through the skin. Transdermal formulations can include patches, ointments, creams, gels, salves, and the like. In some embodiments, the composition is applied topically as a sunscreen.

In some embodiments, the composition is in a dosage form for administration orally. In some embodiments, the dosage form can be a capsule or tablet. Powder forms can also be produced from the liquid extract with the methods taught herein, and the powder can offer even greater ease of consumption when manufactured into dosage forms known to one of skill, such as filled into capsules or compressed into tablets. Powders can also offer greater stability over liquids in some embodiments.

In some embodiments, the extract can be an oil extract or a surfactant extract that may be filled into capsules, or it can be an alcohol extract that may be dried to a powder, and the powder filled into capsules or made into tablets. In some embodiments, the extract can be extracted with an edible oil as an extraction solvent, as the oil extract can be emulsified and is at least substantially non-toxic. Since the extractible components of the root are highly oil soluble, they remain predominantly in the oil phase of the emulsion which aids the stability of the product. The liquid extracts that are filled into capsules are sealed with a gelatin or hydroxypropylmethylcellulose (HPMC) solution, depending on whether the capsule shell is comprised of gelatin or hydroxypropylmethylcellulose. The seal substantially prevents leakage of the liquid from the shell.

In some embodiments, the compositions or formulations can be administered in a sustained release formulation, and the formulation can include one or more agents in addition to the compositions taught herein. In some embodiments, the sustained release formulations can reduce the dosage and/or frequency of the administrations of such agents to a subject.

In some embodiments, the compositions or formulations can be administered in conjunction with at least one other therapeutic agent for the condition being treated. The amounts of the agents can be reduced, even substantially, such that the amount of the agent or agents desired is reduced to the extent that a significant response is observed from the subject. A "significant response" can include, but is not limited to, a reduction or elimination of a symptom, a visible increase in a desirable therapeutic effect, a faster response to the treatment, a more selective response to the treatment, or a combination thereof. In some embodiments, the other therapeutic agent can be administered, for example, in an amount ranging from about 0.1 µg/kg to about 1 mg/kg, from about 0.5 µg/kg to about 500 µg/kg, from about 1 µg/kg to about 250 µg/kg, from about 1 µg/kg to about 100 µg/kg from about 1 µg/kg to about 50 µg/kg, or any range therein. Combination therapies can be administered, for example, for 30 minutes, 1 hour, 2 hours, 4 hours, 8 hours, 12 hours, 18 hours, 1 day, 2 days, 3 days, 4 days, 5 days, 6 days, 7 days, 8 days, 9 days, 10 days, 2 weeks, 3 weeks, 4 weeks, 6 weeks, 3 months, 6 months 1 year, any combination thereof, or any amount of time considered desirable by one of skill. The agents can be administered concomitantly, sequentially, or cyclically to a subject. Cycling therapy involves the administering a first agent for a predetermined period of time, administering a second agent or therapy for a second predetermined period of time, and repeating this cycling for any desired purpose such as, for example, to enhance the efficacy of the treatment. The agents can also be administered concurrently. The term "concurrently" is not limited to the administration of agents at exactly the same time, but rather means that the agents can be administered in a sequence and time interval such that the agents can work together to provide additional benefit. Each agent can be administered separately or together in any appropriate form using any appropriate means of administering the agent or agents. One of skill can readily select the frequency, duration, and perhaps cycling of each concurrent administration.

Having the Curcumin compounds in the form of extracts, dry or liquid, allows for ease of the selection of dose and concentration in dosage forms. A range of other agents or additives may be included to provide additional control over a desired therapeutic effect, cosmetic appeal, or perhaps aid in compliance for a recommended use. Stable, concentrated formulations, such as solutions, emulsions, microemulsions, and nanoemulsions would, for example, potentially increase compliance of administration and bioavailability of the components of the extract after administration. A desirable therapeutic effect can include, for example, increasing bioavailability of the extract through topical use or consumption, providing additional therapeutic effect through addition of a second agent, adjusting the sun protection factor of a sunscreen (spf), and the like. In a sunscreen, for example, the emulsion can be formulated as small globules to provide more complete coverage of the skin. In some embodiments, the globule size can be used to adjust UV protection and improve the stability of an emulsion. A cosmetic appeal can include, for example, providing the extract as a cream or lotion, adjusting the oiliness of a composition, adding a pleasing scent or moisturizer, and the like. Aiding in compliance can include, for example, adjusting the dosage to be in a form that facilitates compliance of patients by offering a small dosage form for consumption by concentrating the extract or, perhaps, offering a time-delay dosage form to reduce the frequency of patient intake that is desired to achieve a particular therapeutic effect.

In some embodiments, a pharmaceutically acceptable composition will comprise a purified and/or isolated liquid extract from the roots of a *Curcuma longa* L. plant. The liquid extract can comprise curcumin; demethoxycurcumin; bisdemethoxycurcumin; or, a combination thereof. The liquid extract also contains an at least substantially non-toxic extraction solvent that removes the extract from the roots of a *Curcuma longa* L. plant in an extraction process; and, functions as a pharmaceutically acceptable carrier; wherein, the extraction solvent was used in the extraction process that removed the extract from the roots of the *Curcuma longa* L. plant and chosen to remain as a component of the pharmaceutically acceptable composition.

In some embodiments, an oily extract can be emulsified using, for example, a surfactant as an emulgent. As such, a pharmaceutically acceptable emulsion comprising a purified liquid extract from the roots of a *Curcuma longa* L. plant can be made. The emulsion can comprise curcumin; demethoxycurcumin; bisdemethoxycurcumin; or, a combination thereof. The emulsion includes an at least substantially non-toxic extraction solvent that removes the extract from the roots of a *Curcuma longa* L. plant in an extraction process; and, functions as a pharmaceutically acceptable carrier having (i) an acute oral toxicity with an LD50 of at least 49,700 mg/kg or (ii) an acute dermal toxicity of at least 5000 mg/kg; wherein, the extraction solvent was (i) used in the extraction process that remove the extract from the roots of the *Curcuma longa* L. plant and (ii) chosen to remain as a component of the pharmaceutically acceptable composition. The emulsion comprises a pharmaceutically acceptable oil; and, an emulgent.

Example surfactants include anionic, cationic, zwitterionic, and nonionic surfactants. An example of cationic surfactants includes sodium dodecylsulfate (SDS). An example of anionic surfactants includes cetylpyridinium bromide. An example of zwitterionic surfactants includes dipalmitoylphosphatidylcholine (lecithin). An example of noninionic surfactants includes polyoxyethylene(4) lauryl ether (BRIJ 30). In some embodiments, SPAN- or TWEEN-type surfactants can be used, including SPAN 60, SPAN 80, TWEEN 60, and TWEEN 80. In fact, any one or any combination of the numerous surfactants known to one of skill can be used to the extent that there is reason to believe that such use would be consistent with the teachings provided herein.

In some embodiments, the pH of the formulations can be adjusted. The pH of the formulations are an improvement over the art, as the pH can be adjusted. In some embodiments, the pH can be adjusted to that of the skin, for example. Since the pH of skin is approximately 4.2 to 5.5, depending on the individual and area of the body, the pH of a topical formulation can range from about 4 to about 6.5 in some embodiments, from about 4.3 to about 5.8 in some embodiments, from about 4.5 to about 5.5 in some embodiments, or any range therein. In some embodiments, the pH can be 3.8, 4.0, 4.2, 4.4, 4.6, 4.8, 5.0, 5.2, 5.4, 5.6, 5.8, 6.0, 6.2, 6.4, 6.6, or any increment of about 0.1 therein.

In some embodiments, the viscosity of the formulations can be adjusted. The viscosity of the formulations is an improvement over the art, as the viscosity can be adjusted. For example, the viscosity can be adjusted by choice of solvent or oil, for example, or temperature used in processing as, generally, temperature effect on viscosity is temporary. In some embodiments, the viscosity can be adjusted by warming a desired oil, as long as the heat is not so high as to cause degradation of the *Curcuma longa* extract. In some embodiments, an oil can be heated up to about 65° C., about 55° C., about 45° C., about 35° C., or any temperature therein in increments of about 1° C.

Storage of the extract can be in dry form or liquid form. In liquid form, the extract can be adjusted for concentration to vary potency. And, whether dry or liquid form, the extracts can be stored in amber bottles for stability.

Administration

Any administration vehicle known to one of skill to be suitable for administration of the compounds, compositions, and formulations taught herein can be used. A "vehicle" can refer to, for example, a diluent, excipient or carrier with which a compound is administered to a subject.

The terms "administration" or "administering" can be used to refer to a method of incorporating a composition into or onto the cells or tissues of a subject, either in vivo or ex vivo to test the activity of a system, as well as to diagnose, prevent, treat, or ameliorate a symptom of a disease or condition. In one example, a compound can be administered to a subject in vivo using any means of administration taught herein. In another example, a compound can be administered ex vivo by combining the compound with cell tissue from the subject for purposes that include, but are not limited to, assays for determining utility and efficacy of a composition. And, of course, the compositions can be used in vitro to test their stability, activity, toxicity, efficacy, and the like. When the compound is incorporated in the subject in combination with one or active agents, the terms "administration" or "administering" can include sequential or concurrent incorporation of the compound with the other agents such as, for example, any agent described above. A composition can be formulated, in some embodiments, to be compatible merely with its intended route of administration.

The compounds can be administered in dosage units. The term "dosage unit" can refer to discrete, predetermined quantities of a compound that can be administered as unitary dosages to a subject. A predetermined quantity of active compound can be selected to produce a desired therapeutic effect and can be administered with a pharmaceutically acceptable carrier. The predetermined quantity in each unit dosage can depend on factors that include, but are not limited to, (a) the unique characteristics of the active compound and the particular therapeutic effect to be achieved, and (b) the limitations inherent in the art of creating and administering such dosage units.

A "pharmaceutically acceptable carrier" is a diluent, adjuvant, excipient, or vehicle with which the composition is administered. A carrier is pharmaceutically acceptable after approval by a state or federal regulatory agency or listing in the U.S. Pharmacopeial Convention or other generally recognized sources for use in subjects. The pharmaceutical carriers include any and all physiologically compatible solvents, dispersion media, coatings, antibacterial and antifungal agents, isotonic and absorption delaying agents, and the like. Examples of pharmaceutical carriers include, but are not limited to, sterile liquids, such as water, oils and lipids such as, for example, phospholipids and glycolipids. These sterile liquids include, but are not limited to, those derived from petroleum, animal, vegetable or synthetic origin such as, for example, peanut oil, soybean oil, mineral oil, sesame oil, and the like.

Suitable pharmaceutical excipients include, but are not limited to, starch, sugars, inert polymers, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. In some embodiments, the composition can also contain minor amounts of wetting agents, emulsifying agents, pH buffering agents, or a combination thereof. Oral formulations, for example, can include standard carriers such as, for example, pharmaceutical grades mannitol, lactose, starch, magnesium stearate, sodium saccharine, cellulose, magnesium carbonate, and the like. See Martin, E. W. Remington's Pharmaceutical Sciences.

As described herein, the compositions can take the form of lotions, creams, suspensions, emulsions, tablets, pills, capsules, powders, sustained-release formulations and the like. In some embodiments, the compositions or formulations can be administered to a subject in any non-parenteral manner known to one of skill whereas, in contrast, a parenteral administration involves piercing the skin or a mucous membrane. Depending on the target tissue, the administration can be topical, oral, ocular, otologic, nasal, urogenital, rectal, dermal, vaginal or otherwise to a mucous membrane. Oral administration, for example, can include digestive tract, buccal, and sublingual administration, and a solid or liquid carrier can be used. One of skill will appreciate that the therapeutic program selected, the agents administered, the condition of the subject, and the effects desired, can affect the administration schedule and program used.

The compositions or formulations can be contained in forms that include tablets, troches, capsules, elixirs, beverages, suspensions, syrups, wafers, chewing gums, gels, hydrogels, and the like. Tablets, pills, capsules, troches liquids and the like may also contain binders, excipients, disintegrating agent, lubricants, glidants, chelating agents, buffers, tonicity modifiers, surfactants, sweetening agents, and flavoring agents. Some examples of binders include microcrystalline cellulose, gum tragacanth or gelatin. Some examples of excipients include starch or maltodextrin. Some examples of disintegrating agents include alginic acid, corn starch and the like. Some examples of lubricants include magnesium stearate or potassium stearate. An example of a chelating agent is EDTA. Some examples of buffers are acetates, citrates or phosphates. Some examples of tonicity modifiers include sodium chloride and dextrose. Some examples of surfactants for micellation or increasing cell permeation include coconut soap, anionic, cationic or ethoxylate detergents. An example of a glidant is colloidal silicon dioxide. Some examples of sweetening agents include sucrose, saccharin and the like. Some examples of flavoring agents include peppermint, chamomile, orange flavoring and the like.

In the digestive tract, for example, a solid can include a pill, capsule, tablet, or time-release technology in some embodiments; and, a liquid can include a solution, soft gel, suspension, emulsion, syrup, elixir, tincture, or a hydrogel. Digestive tract administration can include oral or rectal administration using any method known to one of skill. For buccal, sublingual, and sublabial administration, a solid can include an orally disintegrating tablet, a film, a lollipop, a lozenge, or chewing gum; and, a liquid can include a mouthwash, a toothpaste, an ointment, or an oral spray.

One of skill understands that the amount of the agents administered can vary according to factors such as, for example, the type of disease, age, sex, and weight of the subject, as well as the method of administration. Dosage regimens may also be adjusted to optimize a therapeutic response. In some embodiments, a single bolus may be administered; several divided doses may be administered over time; the dose may be proportionally reduced or increased; or, any combination thereof, as indicated by the exigencies of the therapeutic situation and factors known to one of skill in the art. It is to be noted that dosage values may vary with the severity of the condition to be alleviated, as well as whether the administration is prophylactic, such that the condition has not actually onset or produced symptoms. Dosage regimens may be adjusted over time according to the individual need and the professional judgment of the person administering or supervising the administration of the compositions, and any dosage ranges set forth herein are exemplary only and do not limit the dosage ranges that may be selected.

Articles of Manufacture

Kits that encompass finished, packaged and labelled products are provided. These are articles of manufacture that include the appropriate unit dosage form in an appropriate vessel or container such as, for example, a glass vial or other container that is hermetically sealed. In the case of dosage forms suitable for oral administration, the active ingredient, e.g. one or more agents including a dosage form taught herein, may be suitable for administration topically, orally, rectally, vaginally, or the like. Alternatively, the unit dosage form may be a solid suitable for oral, transdermal, topical or mucosal delivery.

As with any such product, the packaging material and container are designed to protect the stability of the product during storage and shipment. In addition, the articles of manufacture can include instructions for use or other information material that can advise the user such as, for example, a physician, technician or patient, regarding how to properly administer the composition as a prophylactic, therapeutic, or ameliorative treatment of the disease of concern. In some embodiments, instructions can indicate or suggest a dosing regimen that includes, but is not limited to, actual doses and monitoring procedures.

In some embodiments, the instructions can include informational material indicating how to administer a composition for a particular use or range of uses, such as a particular indication taught herein, for example, as well as how to monitor the subject for positive and/or negative responses to the administration.

In some embodiments, kits that contain a combination of topical, oral, rectal, or vaginal dosage forms for administrations to a subject are also provided, as well as instructions for use in some embodiments, as the kits can be designed for physicians, patients, or over the counter use by any subject. In some embodiments, the kit is for protecting a dermal tissue from UVA and UVB exposure, the kit comprising an extract of a *Curcuma longa* L. root in an oral dosage form; an extract of a *Curcuma longa* L. root in a topical dosage form; and, instructions for administration of the topical dosage form, the oral dosage form, or a combination of the topical and oral dosage forms. In some embodiments, the kit is for treating any of the other indications taught herein, such that the kit can have any combination of topical, oral, and rectal dosage forms, and optionally instructions for use. The instructions can be designed for the physician, the patient, or any subject, including, for example, instructions for mixing the components for administration, suggested dilution factors for various target sites, and potential combination therapies for combined administrations, such as topical combined with oral administration. The suggested dilution factors can be selected from the administration ranges taught herein, for example, which can be modified in some embodiments as desired, and incorporated into the compositions.

Without intending to be limited to any theory or mechanism of action, the following examples are provided to further illustrate the teachings presented herein. It should be appreciated that there are several variations contemplated within the skill in the art, and that the examples are not intended to be construed as providing limitations to the claims.

Example 1. Extracting *Curcuma longa* L. Root with Ethanol

A variety of solvents may be used to extract the *Curcuma longa* L. root, and this example shows how the extraction can be done using ethanol.

Preparing Fresh *Curcuma longa* Root for Extraction

The extraction can be done with fresh *Curcuma longa* root, and the root can be prepared as follows:

Material

Fresh *Curcuma longa* root 50 g

Method

1. Wash the fresh root in water to remove any traces of soil or other contaminants;
2. Drain to remove excess water;
3. Pat dry with paper towel;
4. Using a sharp knife or scapel, cut the root into pieces approximately ½ "×½ "; and,
5. Use the moist, freshly-cut root pieces for extraction.

Preparing Dried *Curcuma longa* Root for Extraction

The *Curcuma longa* L. root may have been dried, for example, for storage. The dried root can be prepared for extraction as follows:

Material

Dried *Curcuma longa* root 30 g

Method

1. Wash the dried root in a dish of water to remove any traces of soil or other contaminants, changing the wash water as necessary;
2. Drain the wash water;
3. Add fresh water to cover the roots;
4. Soak overnight;
5. Drain the water and pat dry with paper towel;
6. Using a sharp knife or scapel, cut the root into pieces approximately ½"×½";

7. Use the moist, freshly-cut root pieces for extraction;

Extracting with Ethanol

Ethanol is an efficient extraction solvent, and a process that can be used for extraction is as follows".

Material

Prepared *Curcuma longa* root 50 g

Method
1. Transfer the prepared *Curcuma longa* root to a 250 mL beaker;
2. Pour 90% ethanol into the beaker until it covers the prepared material and there is about 20 mL of ethanol above the level of the prepared root;
3. Cover the beaker to prevent loss of ethanol;
4. Allow to macerate for 24 hours;
5. Decant the clear solvent;
6. Filter the remaining solvent under vacuum Preparing a Dried Extract from the Ethanol Extract The extracts can be removed from the ethanol and stored for use as a dry composition. Moreover, ethanol can only be used in limited amounts topically and orally due to it's level of toxicity.

Material

*Curcuma longa* ethanol extract.

Method
1. The prepared ethanol extract is transferred to the round-bottomed flask of a rotary evaporator;
2. The solution is heated to a maximum temperature of 40° and the condensed ethanol is collected via a condenser for the purpose of re-use in subsequent extractions;
3. The resultant powder is stored in an amber bottle until needed; and,
4. An alternate method is to add water to the ethanol extract (for example, until the ethanol concentration is about 25%) and then freeze drying the mixture.

Back-Extracting the Ethanol Extract into Oil

The extracts can be removed from ethanol, which is toxic and undesirable above certain levels, by back-extracting the ethanol extract into a substantially non-toxic oil, such as an edible oil.

Material 50 mL of an ethanol extract of *Curcuma longa*

Method
1. Transfer 50 mL of ethanol extract to 200 mL separating funnel;
2. Add 50 mL of sesame oil;
3. Shake on a mechanical shaker for 30 minutes;
4. Store the separating funnel upright and allow the liquid layers to separate for approximately 6 hours;
5. Carefully remove the sesame oil layer which can be used in formulations of sunscreen; and,
6. One volume of ethanol may be extracted multiple times for efficient extraction of the ethanol.

While the back extraction method, in principle, may be used to an ethanol extract solution with any immiscible oil, the extraction appears to be more effective when sesame oil or cotton seed oil are used when compared to the use of liquid paraffin or glycerin. The relative effectiveness of the back-extraction using a particular oil can be measured and compared, for example, using a spectrophotometric analysis.

Preparing a Powdered *Curcuma longa* Root for Extraction

The *Curcuma* long L. root can be converted into a powder. Extraction efficiency, for example, may be improved by powderizing the sample prior to extraction.

Material

Dried *Curcuma longa* root

Method
1. Place about 50 gm of dried root pieces into a Wedgewood mortar or other mortar with a rough surface (a glass mortar is unsuitable).
2. With controlled tamping from a pestle, break up the pieces of root into smaller pieces.
3. With firm pressure on the pestle, grind the material into a coarse powder; and,
4. Using a coffee mill or similar laboratory grinder (such as a hammer mill) grind the material into a fine powder The fine *Curcuma* powder can be used for ethanol extraction or extraction with oil as described herein, the advantage of the powder being a much better yield of the sunscreen ingredient, as assessed by the UV spectrophotometric assay of the extract. Extracting the powder with a viscous oil, on the other hand, results in a viscous slurry which is difficult to filter.

Example 2. Extracting *Curcuma longa* L. Root with Sesame Oil

The extracts removed using oils that are at least substantially non-toxic, as discussed herein, can be considered as highly favorable to those in the art, as the extracts can be included directly into topical or oral formulations without the use of additional separation steps that include, for example, removal of the extract from the extraction solvent prior to making an at least substantially non-toxic formulation for use.

Material

Prepared *Curcuma longa* root 50 g

Method
1. Transfer the prepared *Curcuma longa* root to a 250 mL beaker;
2. Pour sesame oil into the beaker until it covers the prepared material;
3. Allow to macerate for 48 hours, with mixing after 24 hours;
4. Decant the clear solvent;
5. Add a second amount of sesame oil to cover the prepared *Curcuma longa* root in the beaker;
6. Allow to macerate for a further 48 hours;
7. Decant the clear solvent;
8. Filter the remaining solvent under vacuum;

This type of extract appears to be a bit more dilute than the ethanol extract but can be incorporated directly into lotions and creams. Moreover, the concentration of the oil extract can be adjusted to a predetermined level by the addition of a calculated amount of dry extract of *Curcuma longa* after the spectrophotometric determination of the concentration of the oil.

Other oily solvents such as liquid paraffin, glycerin, squalene and cotton seed oil may be used although the more viscous solvents, such as liquid paraffin and glycerin, are more difficult to separate from the residual matter.

Example 3. Assessing Extraction Efficiency of Different Solvent Systems

The extraction efficacy of different solvent systems were investigated for extraction of curcumin, deoxy curcumin, bis-deoxy curcumin and possibly other curcumin derivatives and related substances (collectively "curcuminoids" hereafter) from plants of the family Zingerberaceae, especially *Curcuma longa* L. While not intending to be bound by any theory or mechanism of action, it may be desired to utilize the whole extract, since plant components are believed to work together to modulate component activities. Biocompatible solvents were the focus, for at least the reasons set-forth herein, including the ability to use the extract in the liquid form (including the extraction solvent) directly in pharmaceutical formulations that are at least substantially non-toxic and acceptable for human use, topically or orally.

Material

Liquid paraffin (light and heavy), glycerin, sesame oil, ethanol, cotton seed oil, polyethylene glycol (liquid grades including PEG 400), isopropyl myristate (IPM), polysorbate 80 (TWEEN 80) and combinations of these ingredients in 2 and 3 component mixtures with sesame oil, liquid paraffin, and cotton seed oil were tested.

Method

The method for determining the extraction efficiency of various solvents was as follows:
1. The results were obtained in triplicate and used to relate the potency of the various extracts;
2. The ethanol extract as taught herein was used as a control, the extract evaporated to dryness;
3. The ethanol extract was weighed as the dry extract and dissolved in a specific volume of ethanol; and, from this first solution, a series of dilutions of known concentration were made as standard solutions to build a standard concentration curve to compare results;
4. The absorption at the wavelength of maximum absorption (420 nm) was determined for each of the standard solutions and the results were used to construct a standard curve of absorption versus concentration;
5. Aliquots of experimental extracts, in various solvents, were dissolved in ethanol and the absorption of the solution was determined;

The results of extractions that were at least as efficient as the ethanol extraction can be compared in the following table:

| Solvent | Amount Extracted (g/100 mL) | Relative Extraction Efficiency (%) (Ethanol = 100%) |
|---|---|---|
| Ethanol | 6 | 100 |
| IPM | 6 | 100 |
| TWEEN 80:IPM (50:50 mixture by volume) | 6.6 | 110 |
| TWEEN 80:IPM (20:80 mixture by volume) | 7 | 117 |
| TWEEN 80 | 8.3 | 138 |

All extractions were compared to an ethanol extraction as a control, and it's worthy to reiterate that ethanol has limited utility since the dose for internal consumption is limited and it cannot be used undiluted for repeated application to large areas of the skin without side effects.

Otherwise ethanol, sesame oil, and cotton seed oil were found to be desirable. Sesame oil and cotton seed oil, for example, were found to extract reasonable amounts of curcuminoids and could be incorporated directly into formulations such as emulsions for internal or external use. The IPM and TWEEN 80 (and their combinations) were found to be even more desirable, particularly were TWEEN 80 was used, having extraction efficiencies that were up to 38% better than the ethanol extraction. Of the different combinations of TWEEN 80 with IPM, namely 10%, 20%, 30%, and so on . . . up to 90% TWEEN 80 by volume, it was surprisingly found that a combination of either 20% or 50% TWEEN 80 appeared to give the most efficient extractions over other combinations, such as 30% and 40% TWEEN 80. We found, surprisingly, that TWEEN 80 (polysorbate 80 from Croda Inc., Edison, NJ 08837) was a better extraction solvent than generic polysorbate 80. TWEEN 80 HP performed even better than TWEEN 80 (non-HP grade). This is surprising since the manufacturers only claim is that the TWEEN 80 HP contains less impurities, such as peroxides, which may cause irritation at the application site. The higher purity grade is not expected, on a theoretical basis, to have improved extraction ability.

Example 4. Comparing Compositions of Ethanol Extracts to Those Produced Using IPM and TWEEN 80

This example compares the composition of an ethanol extract of *Curcuma longa* L. root to the TWEEN 80 extract and the IPM extracts taught herein. The data compares (i) the total yield of curcuminoids and (ii) the relative proportions of individual curcuminoids.

Material

Prepared *Curcuma longa* root

Method 1. prepare an ethanol extract as taught herein;
2. fractionate the crude extract;
3. isolate the individual components of the mixture;
4. identify the individual curcuminoids using NMR and LCMS and compare to literature values; and,
5. Use TLC and HPLC to compare the ethanol extract with extracts produced using TWEEN 80 and IPM extraction solvents.

Extraction Procedure

Turmeric root (3 g) was ground to a powder as taught herein and extracted overnight with 40 ml of ethanol as taught herein. The extract was filtered through Whatman No. 1 filter paper, and the ethanol was removed using a rotary evaporator to give ~180 mg of crude curcuminoids. The crude extract was kept in an amber glass bottle at room temperature.

Fractionation of Crude Extract

The curcuminoids were further fractionated using silica gel 60 column chromatography with $CH_2Cl_2$/methanol gradient elution. The composition of the mobile phase was varied from 100%: 0 to 90:10% to yield pure fractions of Curcumin (1), Demethoxycurcumin (2), and Bisdemethoxycurcumin (3), as follows:

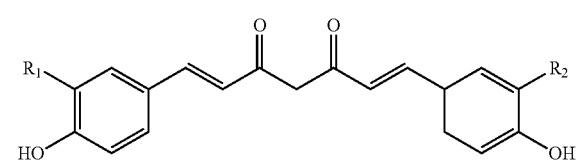

|  |  |  |  |  | Composition of Extract (%) | | |
| --- | --- | --- | --- | --- | --- | --- | --- |
| Compound | $R_1$ | $R_2$ | MW | MF | EtOH | TWEEN 80 | IPM |
| Curcumin (1) | OMe | OMe | 368.38 | $C_{21}H_{20}O_6$ | 71.32 | 73.82 | 70.94 |
| Demethoxycurcumin (2) | OMe | H | 338.35 | $C_{20}H_{18}O_5$ | 18.06 | 17.05 | 18.66 |
| Bisdemethoxycurcumin (3) | H | H | 308.33 | $C_{19}H_{16}O_4$ | 10.62 | 9.13 | 10.4 |

All the fractions and eluates were monitored by thin layer chromatography (TLC) using pre-coated silica gel 60 F254, 0.25 mm glass backed plates (Merck). The spots were detected by spraying with vanillin —$H_2SO_4$ reagent followed by heating. All chemicals and reagents used for TLC were of analytical grade. LC fractions that were tested and showed the same pattern on TLC plates were pooled, and the organic solvent was removed to obtain the individual compounds in powder form for identification and purity testing by additional standard chemical tests.

Identity and Purity Testing

The identity and purity of each curcuminoid was verified using TLC, high-performance liquid chromatography (HPLC)/mass spectrometry and Nuclear Magnetic Resonance (NMR) analyses and by comparing to literature data. See, for example, Masuda, T et al. Phytochemistry 31: 3645-3647 (1992); Syu, W. J. et al. J. Nat. Prod. 61: 1531-1534 (1998); Huang, M. T. et al. Carcinogenesis 16: 2493-2497 (1995); and, Byeoung-Soo Park, et al. J. Agric. Food Chem. 53: 9005-9009 (2005).

NMR $^1$H- and $^{13}$C-NMR spectra were recorded on a BRUKER 600 AV III spectrometer with 5 mm TCI probe using tetramethylsilaneas an internal standard. Chemical shifts are given in δ(ppm).

Mass Spectrometry

Mass spectra were recorded on an AGILENT 1200 Series LC/MSD VL system. MS data were recorded on an Agilent Technology (HP) instrument with 5973 Network Mass Selective Detector (MS model).

HPLC

A reverse phase HPLC method was developed using water:acetonitrile gradient 100:0 to 0:100% over 15 minutes. The purity and identity of the curcuminoids was examined by reverse-phase HPLC (HITACHI, Elite La Chrome) equipped with a photodiode-array detector (L-2455) using isolated pure compounds as a reference. The physico-chemical properties of these compounds are summarized below.

The structures of 1-3 were identified by comparing the spectral data with those reported in the literature. See Id. The following evidence was used for this comparison:

Curcumin [1]
Visual: Orange crystals;
LC-APCIMS (negative): MS, m/z 367; $C_{21}H_{20}O_6$;
HPLC: Retention time 12.41 min
1H NMR (CDCl3) data: δ 7.53 (2H, d, J=16 Hz, HC=C, 1,7-H, alkene, trans), 7.15 (2H, m, 6-ArH), 6.82 (4H, m, 2.5-ArH), 6.61(2H, d, J=16, =CH—CO—, 2,6-H, alkene, trans), 5.91 (1H, s, CH=C(OH)—, 4-H), 3.89 (6H, s, 3-ArOCH 3), ppm;
13C NMR (CDCl$_3$) data: δ 185.0, 184.9, 150.6, 149.6, 142.3, 128.7, 124.3, 122.44, 122.41, 116.7, 111.9, 102.2, 56.6 ppm.

Demethoxycurcumin [2]
Visual: Orange crystals;
LC-APCIMS (negative): MS, m/z 337; $C_{20}H_{18}O_5$; HPLC: Rt 12.20 min 1H NMR (CDCl3) data: δ 7.58 (d, 1H), 7.49 (d, 1H), 7.21 (s, 1H), 7.12 (dd, 1H), 6.84 (d, 2H), 6.61 (t, 1H), 5.95 (br s, —OH), 3.89 (s, 3H, —OCH3)
13C NMR (CDCl$_3$) data: δ 185.1, 184.8, 161.3, 142.3, 142.0, 131.3, 128.7, 124.3, 122.1, 117.0, 116.7, 111.9, 56.6 ppm.

Bisdemethoxycurcumin [3]
Visual: Orange crystals
LC-APCIMS (negative): MS, m/z 307; $C_{19}H_{16}O_4$; Rt 11.99 min 1H NMR (500 MHz, (CDCl$_3$) data: δ 7.57 (d, 2H), 7.49 (d, 4H), 6.82 (d, 4H), 6.59 (d, 2H), 5.92 (s, 1H).
13C NMR (CDCl$_3$) data: δ 84.5, 161.3, 141.5, 131.3, 128.2, 122.1, 117.0, 102.2.

TWEEN 80 and IPM extracts contain the same constituents as the ethanol extract and in approximately the same proportions. The identity and relative proportions of curcuminoids in TWEEN 80 and IPM extracts were determined by HPLC.

Example 5. Yield and Stability of a *Curcuma longa* L Root Extract

Yield: All of the examples taught herein provided a significant yield of extract from the *Curcuma longa* L. root. When the *Curcuma longa* L. was prepared as a powdered root, however, it provided larger yields of the extract from a single extraction. Extraction of 50 g of the powdered root with ethanol, for example, produced about 1.5 gm of dried extract from a single extraction with 50 mL of ethanol. Extraction of the powdered root with sesame oil, and alternatively squalene, also produced reasonable yields.

Stability: All extracts, stored in amber glass bottles, were stable for more than a year when tested by a spectrophotometric method.

Example 6. Formulations Produced Using IPM Extracts, and TWEEN 80: IPM Extracts

The extracts obtained using combinations of TWEEN 80 and IPM can be directly formulated from the liquid extract as an emulsion (creams or lotions) for external use; and, a limited amount of this mixture, or an emulsion produced from it, can be consumed by a human subject. The extracts obtained using IPM are also capable of directly going into formulation for topical or oral administration although, as noted, it can be used with higher amounts of IPM when applied topically, for example, as a sunscreen to the skin. This example provides some formulations for topical and oral use.

A Simple Oil Formulation Made Directly from an Extract Obtained Using IPM Only

| | |
| --- | --- |
| IPM extract | 75 g |
| Sesame oil | 25 g |
| Butylated hydroxytoluene | 0.01 g |
| Citrus extract | 0.1 g |

1. Dissolve butylated hydroxytoluene in IPM extract with stirring. Warm slightly to facilitate dissolution;
2. Add sesame oil and stir without further heating; and,
3. Add citrus extract and stir.

Another formulation . . .

A Lotion Formulation Made Directly from an Extract Obtained Using a Combination of 20% TWEEN 80 and 80% IPM

| | |
|---|---|
| Extract with 20% Tween 80 in 80% IPM | 50 g |
| Span 80 | 4.86 g |
| Water | 45.14 g |
| Rose perfume | 0.1 g |

1. Gently warm the extract to 50° C.;
2. Add the SPAN 80 with continued warming and stir until homogenous (the quantity of SPAN 80 was calculated as described herein; IPM has a required HLB of 11.5);
3. Separately heat the water to 52° C.-54° C.;
4. Add the water all at once with rapid stirring and continue to stir rapidly until emulsion is well formed;
5. Allow to cool with intermittent slow stirring; and,
6. When cooled almost to room temperature, add perfume and stir.

Another formulation . . .

A Cream Formulation Made Directly from an Extract Obtained Using a Combination of 20% TWEEN 80 and 80% IPM

| | |
|---|---|
| Extract with 20% Tween 80 in IPM | 50 g |
| Polawax | 4 g |
| Water | 46 g |
| Lavender perfume | 0.1 g |

1. Gently warm the extract to 50° C.;
2. Add the Polawax with continued warming and stir until wax is evenly dispersed;
3. Separately heat the water to 52° C.-54° C.;
4. Add the water all at once with rapid stirring and continue to stir rapidly until emulsion is well formed;
5. Allow to cool with intermittent slow stirring; and,
6. When cooled almost to room temperature, add perfume and stir.

The extracts can be formulated into emulsions (e.g., for creams and lotions) that contain more than one oil phase ingredient as the following example illustrates. The proportions HLB values of the different oils incorporated are used to compute the overall required HLB for the oil phase. The amount of a second emulgent to be added to the TWEEN 80 can then be easily determined. In the following example, when liquid paraffin, sesame oil, and IPM (which have the required HLBs of 12, 7 and 11.5, respectively) are combined in the proportions given in this formulation, the overall required HLB is found to be 10.5. The addition of an emulgent blend, calculated on a percentage by weight of the total weight of emulgents, is 42% SPAN 80 (HLB=4.3) to 58% TWEEN 80 (HLB=15) and results in a mixture with a desired HLB of 10.5.

Another formulation . . .

An Emulsion Made Directly from an Extract Obtained Using IPM Only, the Emulsion Formulated to Contain Multiple Oil Phase Components

| | |
|---|---|
| Light liquid paraffin | 20 g |
| Sesame oil | 10 g |
| IPM | 5 g |
| Span 80 | 8.4 g |
| Tween 80 | 11.6 g |
| Water | 45 g |
| Rose perfume | 0.1 g |

1. Gently warm the light liquid paraffin and sesame oil to 50° C.;
2. Add the SPAN 80 and, with continued warming, stir until all ingredients are evenly dispersed;
3. Add the TWEEN 80 extract and warm briefly;
4. Separately heat the water to 52° C.-54° C.;
5. Add the water all at once with rapid stirring and continue to stir rapidly until emulsion is well formed;
6. Allow to cool with intermittent slow stirring; and,
7. When cooled almost to room temperature, add perfume and stir.

Another formulation . . .

A Microemulsion Made Directly from an Extract Obtained Using a Combination of 20% TWEEN 80 and 80% IPM

| | |
|---|---|
| Extract with 20%:80% of Tween 80:IPM | 50 g |
| Isopropanol | 20 g |
| Water | 4 g |

1. Combine the extract and isopropanol while stirring (without heating); and,
2. Add the water (no heat) with stirring.

Another formulation . . .

A Microemulsion Intended for External Use Made Directly from an Extract Obtained Using TWEEN 80

| | |
|---|---|
| Extract with TWEEN 80 | 10 g |
| IPM | 40 g |
| Isopropanol | 20 g |
| Water | 4 g |

1. Combine all ingredients with low intensity mixing and without heating; and,
2. The microemulsion is observed as transparent, and the globule size is measured using a dynamic light scattering with a Malvern Nanosizer S and showed a single peak with a maximum of 262.4 nm. The size, monodispersity, ease of formulation without use heat, and clarity of the solution all confirm that it is a microemulsion.

Another formulation . . .

An Edible Emulsion Made Directly from an Extract Obtained Using TWEEN 80

| | |
|---|---|
| Extract with TWEEN 80 | 14.4 g |
| SPAN 80 | 5.6 g |
| Mineral Oil | 20 g |
| Water | 60 g |

1. Heat the mineral oil and SPAN to 50° C.-52° C. and stir gently;
2. Add TWEEN extract and carefully heat to 50° C.-52° C., taking care not to overheat;
3. Stir the mixture until uniform;
4. Heat the water to 52° C.-55° C., and add slowly but all-at-once to the mixture; and,
5. Stir vigorously until the emulsion is well-formed, and then stir occasionally until the emulsion reaches room temperature.

Another formulation . . .

An Edible NANOemulsion Intended to Increase Bioavailability Upon Consumption, the Nanoemulsion Made Directly from an Extract Obtained Using TWEEN 80

| | |
|---|---|
| Extract with TWEEN 80 | 14.4 g |
| SPAN 80 | 5.6 g |
| Mineral Oil | 20 g |
| Water | 60 g |

1. Heat the mineral oil and SPAN to 50° C.-52° C. and stir gently;
2. Add TWEEN extract and carefully heat to 50° C.-52° C., taking care not to overheat;
3. Stir the mixture until uniform;
4. Heat the water to 52° C.-55° C., and add slowly but all-at-once to the mixture;
5. Stir vigorously until the emulsion is well-formed, and then stir occasionally until the emulsion reaches room temperature; and,
6. Pass the emulsion repeatedly through a microfluidizer to reduce globule size to below 200 nm.

The microfluidizer can be sensitive to viscosity, and viscosity can be adjusted, for example by (i) adding water; (ii) decreasing the oil phase; or (iii) a combination thereof. The content of extract should be kept high, which can be done by keeping the TWEEN phase high in this example, as that's the source of the extract.

Non-aqueous liquids, such as extracts in TWEEN 80 or oils, or blends of TWEEN 80 extracts with compatible absorption-enhancing liquids (such as polyethyleneglycol 400), or mixtures of liquid extracts and molten solids (such as GELUCIRE or solid polyethylene glycol, for example, polyethylene glycol 4000) may be filled into two piece gelatin capsules and sealed to prevent leakage of the liquid fill from the capsules. The sealing is performed using equipment such as the QUALICAPS HARD-CAPSULE-BAND-SEALING machine. The capsules, filled with the extract, are placed on slats appropriate for the size of capsule. The machine draws the metal slat containing the capsules through the machine applying a thin film of the sealing material (gelatin or hydroxypropylmethylcellulose (HPMC) solution, depending on whether gelatin or hydroxypropylmethylcellulose capsules are used). In a second passage through the machine, the seal is trimmed so that, effectively, a narrow band of sealing material is applied. Examples of the method of preparation of the sealing solutions are as follows:

Another example for preparing a dosage form . . .

Preparation of Gelatin Solution for Capsule Sealing
1. Measure 750 mL of ddH$_2$O (double-distilled water) into a clean 1 L beaker and heat the water to 57-60° C.;
2. Add the dye to the water, stir until the dye is completely dissolved and a uniform solution is formed, and heat to 57-60° C.;
3. Weigh 503 g of above water (57-60° C.) into a fresh 1 L beaker (tared to zero);
4. Add 0.6 g of Tween-80 to the above beaker;
5. Weigh 141 g of gelatin into a tared weighing boat;
6. Add gelatin to the above beaker with hand stirring (spatula or mixing rod);
7. Continue stirring until gelatin spreads evenly in the solution. Cover the beaker with aluminum foil;
8. Place the beaker in an oven (preheated to 55° C.). Mix every 20-30 min, to prevent gelatin from sedimenting at the bottom; and,
9. Continue mixing until all the gelatin is dissolved and a clear uniform solution is formed (2-3 hr).

Another example for preparing a dosage form . . .

Preparation of HPMC Solution for Capsule Sealing
1. Weigh 100 g of HPMC powder into a fresh 1 L beaker (tared to zero);
2. Weigh 344 g of absolute ethanol and add in increments to HPMC powder with continuous hand mixing (use spatula or knife). Mix for about 20-30 min until a smooth paste is formed (no clumps or dry HPMC powder);
3. Add 181 gm of ddH$_2$O to above HPMC paste (HPMC+Alcohol) with continuous hand mixing (no heating is required);
4. Add the dye to the water, stir until the dye is completely dissolved and a uniform solution is formed; and,
5. Continue mixing until a clear solution is formed (15-20 min). Once a clear solution is formed, cover the beaker with parafilm, and let it stand for at least an hour prior to use (for air bubbles to dissipate).

Another example for preparing a dosage form . . .

Suppository and Pessary Formulations

Suppository and pessary formulations for administration, respectively, to the rectum or vagina of a subject may be prepared by combining, for example, the Tween 80 extract or the oil extract with a suitable suppository or pessary base. In the molten state, the combined base and extract are poured into suitable molds which are available commercially. When solidified, the suppositories are removed from the mold. Examples of suppository bases include Gelucire and polyethylene glycol. When the base is available in various melting point grades, and is expected to melt to release the active ingredient, a blend of grades may be used such that the suppository or pessary melts at body temperature. Administration of the extracts by these routes and others, which do not include the swallowing of the dosage form, is expected to lead to higher absorption of the drug since the degradation in the gastro intestinal tract and liver are avoided.

Examples of bases that could be used are gelatin, cocoa butter, polyethylene glycols, polyvinyl pyrrolidone, gelatin/glycerin combinations, esterfied fatty acids, polyoxyethelene sorbitans and polyoxyethylene sorbitan fatty acid esters. Various additives may be incorporated including surfactants and absorption enhancers such as medium chain (C8 to C12) fatty acids and fatty acid esters. Various commercial bases, which may contain mixtures of different components, are sold under the trade names lmhausen, Witepsol and Gelucire. Various grades of each of these are available for specific applications. Mixtures of various bases may also be utilized in order to obtain a suppository or pessary with the required properties. Other shaping methods for forming the suppositories or pessaries including cold molding and compression may also be used.

Example 7. Preparing a Sunscreen Lotion Containing *Curcuma longa* L Root Extract An emulsion of an extract of *Curcuma longa* L. can be produced in sesame oil using non-ionic surfactants, for example. A surfactant, or surfactant pair, should first be chosen with the correct solubility for the application. For non-ionic surfactants, we can calculate the hydrophilic-lipophilic balance (HLB) to match the HLB to the application.

Calculating Surfactant Ratio to Obtain Desired HLB

The HLB is the hydrophile-lipophile balance and gives an indication of the solubility of a surfactant.

The first step is to select a surfactant or surfactant pair. A desirable surfactant or surfactant pair can be any surfactant or surfactant pair thought by one of skill to be useful in creating the emulsions that can be used with the teachings provided herein. A SPAN surfactant and a TWEEN surfactant can be considered a desirable surfactant pair to create an emulsion of *Curcuma longa* L. extract in sesame oil. A SPAN surfactant, for example, can be referred to as a sorbitan alkanoate, and SPAN 60 has an HLB of 4.7. A TWEEN surfactant, for example, can be referred to as an ethoxylated sorbitan alkanoate, and TWEEN 60 has an HLB of 14.9.

The following procedure can be used to calculate the relative percentages of SPAN 60 and TWEEN 60 to be used in an emulsion with sesame oil to determine the ratio of surfactants to obtain the desired HLB:

1. The desired HLB of sesame oil for oil-in-water emulsions has been published as 7.0. See, for example, Haus, editor. Oral Lipid-based Formulations: Enhancing the Bioavailability of Poorly Water-Soluble Drugs. Informa Healthcare USA, Inc., New York, NY (2007).
2. If the fraction of SPAN 60=x,
3. Then, the fraction of TWEEN 60=1−x. Solving for x . . .

$x(4.7)+(1-x)14.9=7$; and, $x=0.775$

As such, this means that a desired emulsion in this case should be successfully prepared using a mixture of 77.5% SPAN 60 and 22.5% TWEEN 60 to obtain the 7.0 HLB for the mixture.

Making an Emulsion and Starting with a Sesame Oil Extract of *Curcuma longa* L.

An effective emulsion of a sesame oil extract can be made as follows:

Materials
1. Extract a *Curcuma longa* L. root as described herein;
2. Assume 200 g total weight of the emulsion;
3. Weigh 60 g of the sesame oil extract;
4. Assume 6% by wt of the surfactant pair, SPAN 60/TWEEN 60, HLB 7.0, and combine 9.3 g SPAN 60 with 2.7 g TWEEN 60 accordingly; and,
5. Weigh 128 g water for the remainder.

Method
1. Carefully heat the sesame oil extract in a beaker to about 50° C., being careful not to overheat;
2. Add the SPAN 60 and stir with a glass rod to dissolve;
3. Separately, preheat the water to approximately 55° C.;
4. Add the TWEEN 60 to the water and stir with a glass rod to dissolve;
5. Add the water with TWEEN 60 to the oil phase ingredients while rapidly stirring the oil using a propeller stirrer. Stir rapidly until emulsion forms, then stir occasionally until cool; and,
6. Pack the lotion in an amber glass bottle.

The above is a basic formulation to which antioxidants, additional emollients, vitamins, etc., may be added as desired. As an alternate way of producing the sunscreen lotion, a dry extract of *Curcuma longa* may be incorporated into a lotion.

Making an Emulsion and Starting with a Dried Extract of *Curcuma longa* L.

Materials

Dried *Curcuma longa* extract as described herein.

Method
1. Weigh 25 mg of dried extract into a small, tared beaker;
2. Add approximately 100 g of sesame oil to the beaker;
3. Using a magnetic stirrer, stir the solution overnight until all the powder is dissolved; and,
4. Use this oily solution to prepare an emulsion as described herein.

Example 8. Novel Broad Spectrum Performance of *Curcuma longa* L. Root Suncreen as Compared to State of the Art Suncreens The performance of current state-of-the-art sunscreen chemicals were compared to that of the *Curcuma longa* L. extract in this example.

Figure 1B:
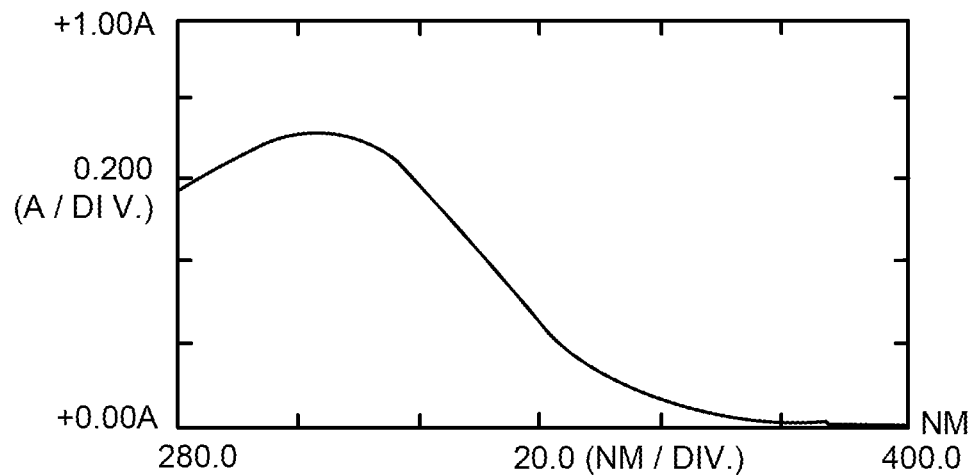
Figure 1C:
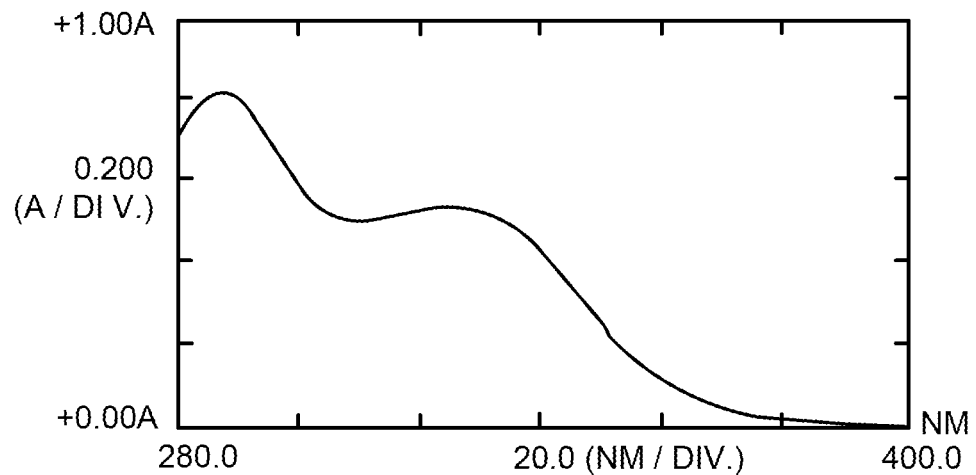
Figure 1D:
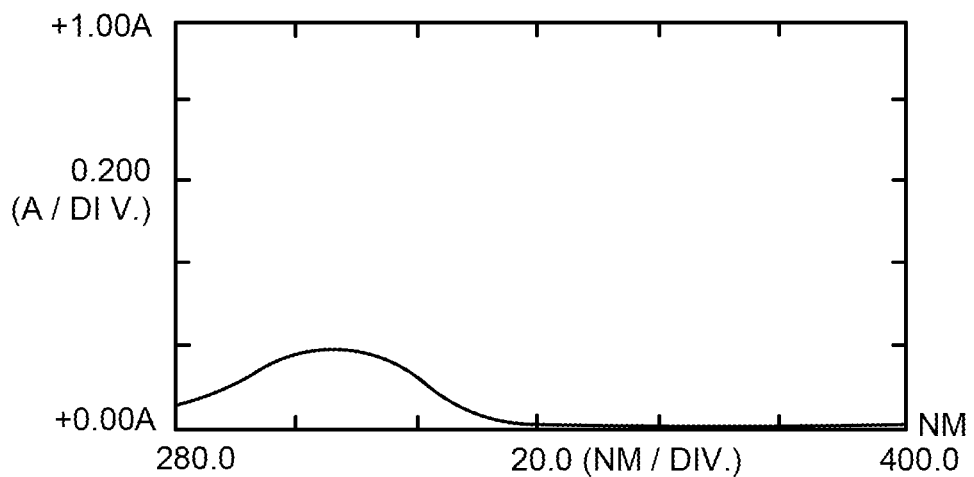
Figure 1E:
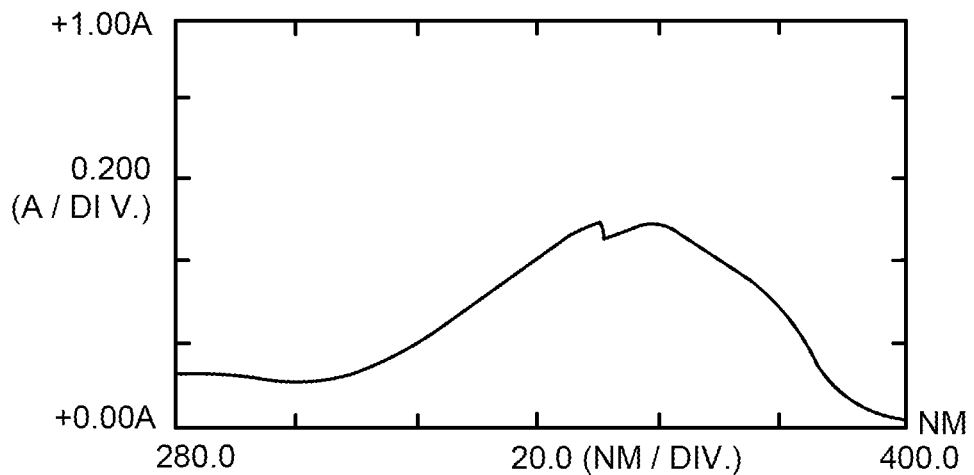

FIGS. 1A-1F compare the absorption spectra of representative current state-of-the-art sunscreen agents to the absorption spectra of *Curcuma longa* L., according to some embodiments. FIG. 1A shows the absorption spectrum of octyl methoxycinnamate at a concentration of 5 ug/ml methanol, FIG. 1B shows the absorption spectrum of octocrylene at a concentration of 0.5 ug/ml methanol, FIG. 10 shows the absorption spectrum of oxybenzone at a concentration of 1 ug/ml methanol, FIG. 1D shows the absorption spectrum of homosalate at a concentration of 20 ug/ml methanol, and FIG. 1E shows the absorption spectrum of avobenzone at a concentration of 5 ug/ml methanol.

The representative sunscreen agents show peaks in the absorption spectrum between the wavelengths of 290 nm to 400 nm which is the range of interest. Ideally, a desired agent would absorb energy across the entire range of 290 nm to 400 nm. In FIGS. 1A-1E, for example, a variety of peak positions are seen in the representative agents, where a high (desirable) absorption can be shown at the wavelength of the peak but there is usually a low or zero absorption at the trough, which is, of course, undesirable. Even combinations of sunscreen agents with peaks and troughs may leave areas within the wavelength range that are not covered, leaving wavelengths for which there is little or no UV protection, an undesirable situation.

FIG. 1A shows that octyl methoxycinnamate has practically no absorption at wavelengths higher than approximately 350 nm. FIG. 1B shows that octocrylene has an absorption that is very low above about 370 nm and is practically zero beyond about 380 nm. FIG. 10 shows that oxybenzone has an absorption that is practically zero above about 380 nm. FIG. 1D shows that homosalate has an absorption that is practically zero above about 340 nm. FIG. 1E shows that only avobenzone has a broad spectrum of activity but it, too, has low absorption beyond about 390 nm.

Figure 1F:
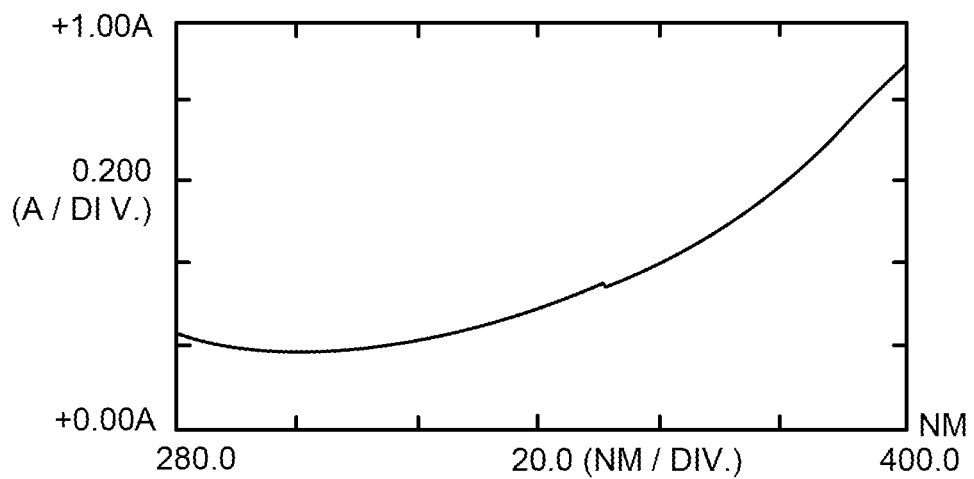

FIG. 1F, on the other hand, shows the very broad spectrum of absorption of the *Curcuma longa* L. extract, according to some embodiments. The scan of the extract of *Curcuma*

*longa* shows no dips or troughs in the absorption of UV light from the wavelength of 280 nm to 400 nm. In essence, it was surprising and unexpected to find that *Curcuma longa* L. extract provided such a broad range of protection from the harmful rays of the sun across the entire wavelength range for which humans need sunscreen protection.

As seen from FIG. 1F, the UV absorption spectrum extends across the entire range from 280 nm to 400 nm. Moreover, unlike the other agents tested, the level of absorption does not decrease as it approaches the higher UV range but, rather, it surprisingly increases. The UV absorption of the *Curcuma longa* L., for example, covers all of the important UVA region and, moreover, the level of $UVA_1$ absorption is high rather than minimal at best, as with state-of-the-art sunscreens. As such, the *Curcuma* long L. is a much superior sunscreen agent when compared to the representative sunscreen agents using at least the criteria of the Jun. 17, 2011, the FDA report discussed herein. Restated in this section for emphasis, the FDA stated that (i) sunscreen products should have both UVA and UVB protection; and, (ii) the UVA range has two unique areas of interest:
the $UVA_1$ area ranging from 340 nm to 400 nm; and,
the $UVA_2$. area ranging from 320 nm to 340 nm.

The FDA also stated that too much emphasis has been placed on UVB, that at least 20% of the protection should be in the $UVA_2$ region, and at least 60% of the protection should be in the $UVA_1$ region, stressing the relative importance of $UVA_1$ region. Accordingly, the UV absorption spectrum of the extract of *Curcuma longa* is not only unique, but also highly desirable when compared to the state-of-the-art sunscreen agents currently in use.

The performance of the extract as a sunscreen was quite surprising, particularly due to the broad spectrum of protection from the sun without requiring use of chemical additives such as $TiO_2$ to screen both UVA and UVB. It should be appreciated that the very broad UV absorption peak of the present extract, covering $UVA_1$, $UVA_2$ and UVB, is unique in the art and offers better protection than multiple compounds that cannot cover this broad UV wavelength range. One of skill will appreciate that, even when multiple sunscreen agents are used, each of the agents can demonstrate its own peak across the absorption spectrum, the result being that the combined agents still contain areas of poor UV absorption.

By the addition of small amounts of blue and red color, the natural color of the extract can be made into a tan color. When applied to the skin of a darker person, this color blends with the skin color and has no further impact on appearance. However, when applied to a fair-skinned person, it will produce a "tanned" appearance. It is possible for one skilled in the art, to produce a range of shades acceptable to fair-skinned persons of different skin tones which, simultaneously, protects from the UV radiation of the sun and offers a tanned appearance. It is also possible for one skilled in the art to add a natural plant extract which has a blue/purple color (such as blueberry extract) to attain the same skin tone effect. The advantage of the latter method is that the chosen natural extract may add additional value to the product, such as, in the case of blueberry extract, a second source of antioxidants which complement the antioxidant effect of the curcumin extract.

Example 9. Method of Testing Sunscreen Formulations on Human Subjects

The methods provided in this section are in accord with the methods detailed in the FDA's final rule on sunscreen preparations and testing published in 21 CFR 352.70(a), dated 17 Jun. 2011 ("regulations" hereafter).

Subjects

Thirteen (13) subjects can be enrolled with the objective of having at least 10 subjects complete the study. Compared to systemically-absorbed drug evaluation studies which, often, involve some drug side effects, the dropout rate for this study is not expected to be high. The referenced FDA guidelines state that at least 10 subjects are needed for valid results.

Exclusion Criteria

Exclusion criteria include the following:

1. Previous history of extreme sensitivity to sunlight with severe sunburn occurring with short exposure; or abnormal responses to sunlight, such as a phototoxic or photoallergic response with normal exposure;
2. Taking medication (topical or systemic) that is known to produce abnormal reactions to light;
3. Uneven skin tones on the areas of the back to be tested;
4. Any lesions on the area of exposure;
5. Tattoos or scarring on the area of exposure;
6. Diabetics; and,
7. Pregnant women.

Inclusion Criteria

Male and female subjects who are fair skinned shall be selected based on their classification, using the following guidelines, as skin types I, II, and III. The classification depends on the response of the fair skinned people to the first 30 to 45 minutes of sun exposure after a winter season of no sun exposure:

1. Always burns easily; never tans (sensitive);
2. Always burns easily; tans minimally (sensitive);
3. Burns moderately; tans gradually (light brown) (normal);
4. Burns minimally; always tans well (moderate brown) (normal);
5. Rarely burns; tans profusely (dark brown) (insensitive); and,
6. Never burns; deeply pigmented (insensitive).

Subject Selection

Subjects will be selected from a pool of volunteers, each of which provide legally effective written informed consent. A medical history will be taken from all subjects with emphasis on the effects of sunlight on their skin. The general health of the individual will be ascertained by means of a physical examination. In addition, the test site will be inspected with emphasis on exclusion criteria 3, 4, 5. The presence of nevi, blemishes, or moles will be acceptable if, in the physician's judgment, they will not interfere with the study results. Excess hair on the back is acceptable if the hair is clipped. Shaving is unacceptable since too much epidermis may be removed.

Trial Materials

The trial materials will consist of:

1. TEST MATERIAL—the sunscreen cream or lotion containing the *Curcuma longa* L. extract as the sun screen material (TEST); and,
2. REFERENCE STANDARD—the standard consists of a cream containing 7% padimate 0 and 3% oxybenzone as the sunscreen materials.

(REFERENCE). The composition of the reference standard is given as follows in the regulations*:

| Ingredients | % by weight |
|---|---|
| Part A | |
| Lanolin | 4.50 |
| Cocoa butter | 2.00 |
| Glyceryl monostearate | 3.00 |
| Stearic acid | 2.00 |
| Padimate O | 7.00 |
| Oxybenzone | 3.00 |
| Part B | |
| Purified water USP | 71.60 |
| Sorbitol solution | 5.00 |
| Triethanolamine 99 percent | 1.00 |
| Methylparaben | 0.30 |
| Propylparaben | 0.10 |
| Part C | |
| Benzyl alcohol | 0.50 |
| Part D | |
| Purified water USP | QS to 100 g |

Federal Register/Vol. 76, No. 117/Friday, Jun. 17, 2011: Labeling and Effectiveness Testing; Sunscreen Drug Products for Over-the-Counter Human Use.

Method of Making REFERENCE

The method can be performed as follows:

1. Add the ingredients of Part A into a suitable stainless steel kettle equipped with a propeller agitator. Mix at 77 to 82° C. until uniform;
2. Add the water of Part B into a suitable stainless steel kettle equipped with a propeller agitator and begin mixing at 77 to 82° C. Add the remaining ingredients of Part B and mix until uniform;
3. Add the batch of 1 to the batch of 2 and mix at 77 to 82° C. until smooth and uniform. Slowly cool the batch to 49 to 54° C.;
4. Add the benzyl alcohol of Part C to the batch of 3 at 49 to 54° C. Mix until uniform. Continue to cool batch to 35 to 41° C.;
5. Add sufficient water of Part D to the batch of 4 at 35 to 41° C. to obtain 100 grams of SPF standard. Mix until uniform. Cool batch to 27 to 32° C.

UV Light Source for Human Testing

This study will use a solar simulator that conforms to the regulations. The simulator should be capable of providing UV radiation such that:

1. UVA II (320-340 nm) should equal or exceed 20 percent of the total UV (290 nm-400 nm) irradiance;
2. UVA I (340 nm-400 nm) should equal or exceed 60 percent of the total UV (290 nm-400 nm) irradiance;
3. The total irradiance limit should be 1500 W/m 2; and,
4. The total irradiance range should be 250-1400 nm.

Method of Human Testing

The method can be performed as follows:

1. The test location will be on the back of the subject between the beltline and the shoulder blade (scapulae) and lateral to the midline. This is the area where the subject's natural sensitivity to UV radiation will be determined, the sunscreen and standard will be applied and assessed;
2. Assessment of the standard and test will be based on the principle of minimal erythemal dose (MED) i.e. the lowest dose of UV radiation that will cause erythema. Firstly, MED will be assessed on the patient's skin with no application of any agent (unprotected) in order to obtain his base-line or control MED. Thereafter, the test formulation and the standard formulation will be applied and the MED determined again.
3. Within the test location, each area for applying a product or the standard sunscreen ("test site") will be outlined with ink. Each test site will be a minimum of 30 cm$^2$ in area. If the person is to be tested in an upright position, the lines will be drawn on the skin with the subject upright. If the subject is to be tested while prone, the markings will be made with the subject prone. Thus stretching and wrinkling of the skin will not alter the extent of the area to which TEST and STANDARD are applied.
4. Each test site area will be further divided into four or five subsites that each have an area of at least 0.5 cm$^2$. The distance between subsites is at least 0.8 cm.
5. Both the test sunscreen product and the standard sunscreen are applied to their respective test areas at a standardized rate. The rate specified in the regulation is 2 milligrams per square centimeter. The density of the formulations will first be determined and the standard weight will be added volumetrically using a suitably sized syringe.
6. Sunscreen drug products and the test product will be evaluated in the same study. These products will be applied in a blinded, randomized manner. Each product will be spread using a finger cot. Presaturation of finger cot is not required.
7. After applying a product, a waiting period of at least 15 minutes is required before exposing the test site areas to radiation.
8. Next, each test subsite within a test site area is be subjected to a specified dosage of UV radiation. A series increasing UV radiation exposures is used for the determination of the MED.
9. In order to maintain the blind, the person who evaluates the MED responses is not the same person who applied the sunscreen drug product to the test site or administered the doses of UV. In addition, care is taken that the evaluator does not know this information.
10. After UV radiation exposure from the solar simulator is completed, the subject's immediate responses to the exposure are recorded. It is important to include all responses. Examples of immediate responses include the following:
    a. darkening or tanning, typically greyish or purplish in color, fading in 30 to 60 minutes, and attributed to photo-oxidation of existing melanin granules;
    b. immediate reddening, fading rapidly, and viewed as a normal response of capillaries and venules to heat, visible and infrared radiation; and,
    c. an immediate generalized heat response, resembling prickly heat rash, fading in 30 to 60 minutes, and apparently caused by heat and moisture generally irritating to the skin's surface.
11. After the immediate responses are noted, shield the exposed area of each subject from further UV radiation for the remainder of the test day.
12. The MED is determined 22 to 24 hours after exposure and the determination is made under the following conditions:
13. The source of illumination is either a tungsten light bulb or a warm white fluorescent light bulb that provides a level of illumination of 450 to 550 lux at the test site
14. The subject should be in the same position used when the test site was irradiated.

15. Determine the smallest dose of energy, for each series of exposures, which produces redness. To be counted, the redness must reach the borders of the exposure site at 22 to 24 hours post exposure. Somewhat more intense erythemas must also be produced, in order to know the minimal dose that produced erythema. The goal is to have some exposures that produce absolutely no effect, some that have redness reaching the borders of the exposure site (and can therefore be counted as minimal exposure producing the required effect) and some exposures that produce a greater effect than is needed (which will not be counted).
16. Reject the test data if the exposure series fails to elicit an MED response on either the treated or unprotected skin sites, or if the responses on the treated sites are randomly absent (which indicates the product was not spread evenly).

Definitions for Human Testing

MED—minimal erythema dose—The MED is the smallest UV dose that produces perceptible redness of the skin (erythema) with clearly defined borders at 16 to 24 hours after UV exposure.

MEDu—the MED for unprotected skin—This is determined on a test site that does not have sunscreen applied.

MEDp—the MED for protected skin—This is determined on a test site that has sunscreen applied ssMEDp—the MEDp for the sunscreen standard tpMEDp—the MEDp for the sunscreen test product Evaluation of test subsites—In order that the person who evaluates the test subsites is not biased, he/she should not be the same person who applied the sunscreen drug product to the test site or administered the UV doses.

Immediate Responses—After UV doses are administered, all immediate responses should be recorded. These may include an immediate darkening or tanning, typically grayish or purplish in color, which fades in 30 to 60 minutes; an immediate reddening at the subsite, due to heating of the skin, which fades rapidly; and an immediate generalized heat response, spreading beyond the subsite, which fades in 30 to 60 minutes MED Determination—After the immediate responses are noted, each subject should shield the exposed area from further UV radiation until the MED is determined. This must be determined 16 to 24 hours after UV exposure i.e. the final MEDu, ssMEDp, and tpMEDp are typically determined the day following determination of the initial MEDu. Evaluate the erythema responses of each test subsite using either tungsten or warm white fluorescent lighting that provides at least 450 lux of illumination at the test site. For the evaluation, the test subject should be in the same position as he or she was when the test site was irradiated.

SPF Determination—

1. Calculate an SPF value for each test subject or individual (SPFi) as follows:

$$SPFi = \frac{MEDp}{MEDu}$$

2. Calculate the MEAN SPF and the standard deviation (s) from the SPFi values. Calculate the standard error (SE), which equals $s/\sqrt{n}$ (where n equals the number of subjects who provided valid test results). Obtain the t value from Student's t distribution table corresponding to the upper 5-percent point with n−1 degrees of freedom. Determine the labeled SPF value, which equals the largest whole number less than MEAN SPF−(t*SE)

3. In order for the SPF determination of a test product to be considered valid, the SPF value of the SPF standard should fall within the standard deviation range of the expected SPF (i.e., 16.3±3.43).

Example 10. Testing the Anti-Oxidant Activity of the *Curcuma longa* L. Extract

The antioxidant activity of *Curcuma longa* L. was assessed and compared to resveratrol, a well-known antioxidant.

Material

A TWEEN extract of *Curcuma longa* produced as taught herein; Resveratrol (trans-3,5,4'-trihydroxystilbene), is an extract of the skin of red grapes and found in red wines.

Method

The comparisons were done using the DPPH (1,1-diphenyl-2-picrylhydrazyl) assay, a well-established method for testing antioxidant activity. The DPPH assay is based on the inhibition by antioxidants of the absorbance of the DPPH free radicals, having a characteristic absorption spectrum showing a maximum at 517 nm.

The resveratrol is dissolved in methanol, and both the TWEEN extract and resveratrol were tested at the same concentration of 4.2 mg/mL.

A 50 µM DPPH-free radical solution was prepared by dissolving the 1,1-diphenyl-2-picrylhydrazyl in methanol.

1. The absorbance of DPPH-free radical solution (prepared as above) was read at 517 nm (control);
2. 0.1 mL of Tween extract of *Curcuma longa* was diluted with 0.4 mL of methanol;
3. 2 mL of DPPH reagent was added and its absorbance was read after allowing 60 seconds reaction time, using 0.1 mL of Tween diluted with methanol as a blank;
4. The absorbance of solution 3 was read at 60-second intervals using an automated function on the spectrophotometer;
5. A solution of resveratrol (4.2 mg/mL) was prepared;
6. 0.1 mL of the resveratrol solution was diluted with 0.4 mL of methanol and 2 mL of DPPH reagent was added and the absorbance of this solution was read after allowing 60 seconds reaction time, using methanol as a blank;
7. The absorbance of solution 6 was read at 60-second intervals using an automated function on the spectrophotometer; and,
8. The % inhibition of DPPH-free radicals was calculated using the following equation, where A is absorbance, the control is DPPH, and the samples are the TWEEN extract and the resveratrol:

% inhibition=$[A_{control}-A_{sample}]/A_{control}]\times 100$

Figure 2A:
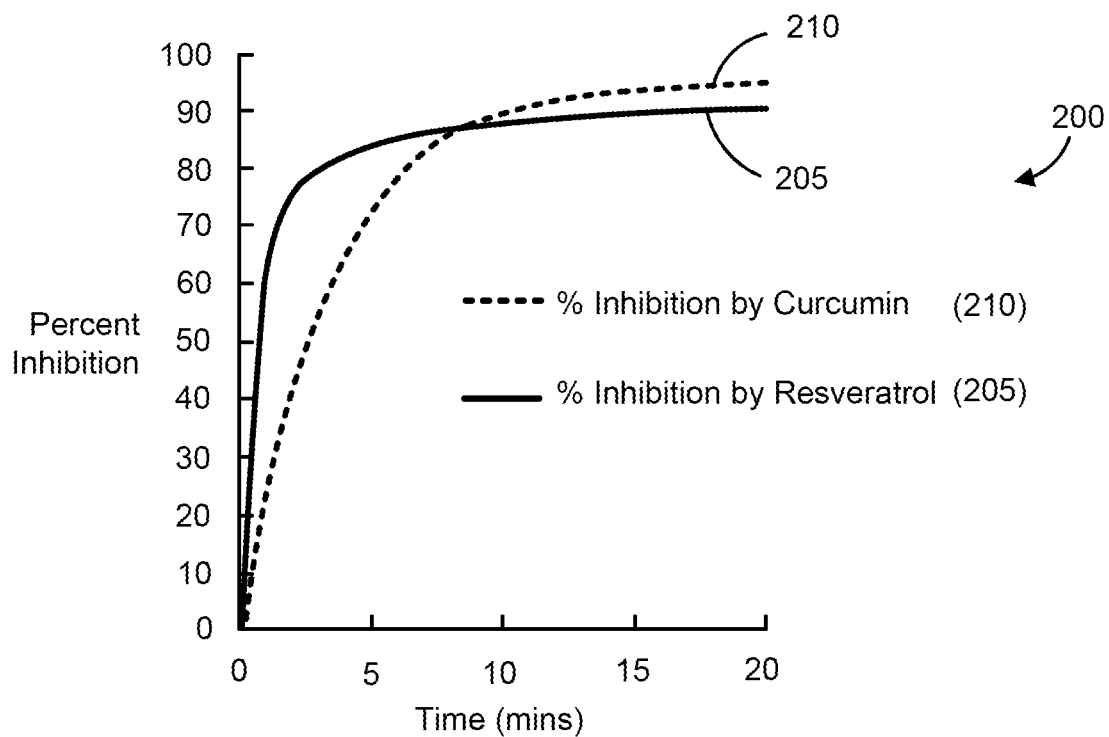
FIGS. 2A and 2B compare the antioxidant activity of the TWEEN extract of Curcumin *longa* to the antioxidant activity of resveratrol, according to some embodiments.
Figure 2B:
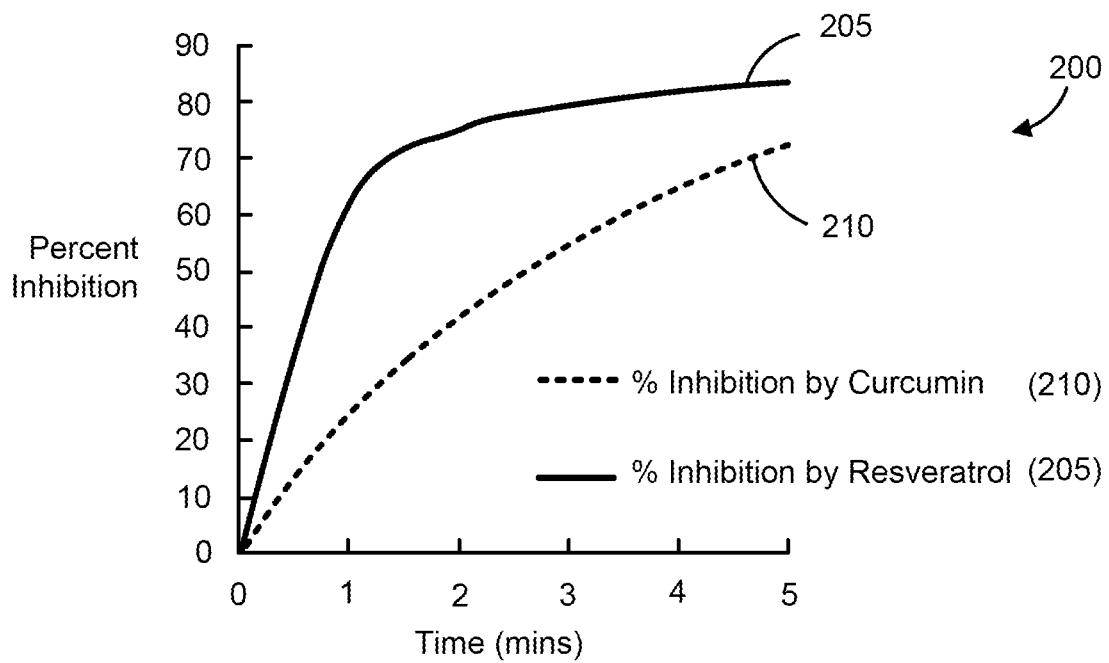

FIGS. 2A and 2B compare the antioxidant activity of the TWEEN extract of Curcumin *longa* to the antioxidant activity of resveratrol, according to some embodiments. FIG. 2A shows the comparison 200 over a time frame of 20 minutes, where it can be seen that the antioxidant activity of the TWEEN extract 205 and the resveratrol 210 is comparable at times exceeding 5 minutes. FIG. 2B shows the comparison over the time frame of 5 minutes, where it is clear that the activity of TWEEN extract 205 is multiples higher than the resveratrol 210 for the first couple of minutes, and the activities for the TWEEN extract 205 and the resveratrol 210 become comparable at times ranging from about 5 minutes to about 20 minutes.

As such, it can be concluded that the antioxidant activity of the TWEEN extract is comparable to a well-known antioxidant having an accepted and desirable activity that provides accepted and desirable therapeutic results. Resveratrol has shown to be promising at preventing and/or treating at least the following:

1. cancer in animals;
2. reducing the risk of heart disease by inhibition of vascular cell adhesion, inhibition of vascular smooth muscle cell proliferation, inhibition of platelet aggregation, inhibition of LDL peroxidation, stimulation of endolethelial nitric oxide synthase (eNOS) activity;
3. diabetes, through it's hypoglycemic and hypolipidemic effects, and it also ameliorates common diabetes symptoms, such as polyphagia, polydipsia, and body weight loss;
4. neuroprotective effects, including reducing plaque formation in brains, a component of Alzheimer's disease and other neurodegenerative diseases
5. anti-inflammatory effects, including inhibiting both acute and chronic phases of the inflammatory process, and showing promise as a potential therapy for arthritis, for example, the progression of inflammatory arthritis.
6. antiviral effects, including inhibiting herpes simplex virus (HSV) types 1 and 2 replication by inhibition of an early step in the virus replication cycle, inhibiting HSV replication in the vagina, limiting extravaginal disease, as well as inhibiting varicella-zoster virus, influenza viruses, respiratory viruses, and human cytomegalovirus. It's also has shown synergistic enhancements in the treatment of the anti-HIV-1 activity of several anti-HIV drugs.
7. Testosterone level, including increasing hormone level and sperm count.

As such, given the comparative antioxidant activity provided in this example, in addition to the literature on *Curcuma longa*, this suggests that the extracts of Curcumin *longa* may be promising in treating at least these conditions as well.

We claim:

1. A method of preparing a formulation acceptable for oral administration having a pharmaceutically acceptable liquid extract of *Curcuma*, the method comprising:
    macerating at least a portion of a *Curcuma* root for an effective time in an at least substantially non-toxic extraction solvent that includes a component selected from the group consisting of sesame oil, liquid paraffin, glycerin, squalene, cotton seed oil, liquid-grade polyethylene glycol, isopropyl myristate, polysorbate 80, a sorbitan alkanoate, an ethoxylated sorbitan alkanoate, and combinations thereof;
    separating the extraction solvent from the macerated *Curcuma* root to create a liquid extract of *Curcuma*, the extract including curcumin; and,
    incorporating the liquid extract directly into the formulation without removal of the extraction solvent, the carrier having the acute oral toxicity with the LD50 of at least 49,700 mg/kg which is at least substantially less toxic than ethanol.
2. The method of claim 1, wherein the extraction solvent comprises polyoxyethylene (20) sorbitan monooleate.
3. The method of claim 1, wherein the extraction solvent comprises isopropyl myristate.
4. The method of claim 1, wherein the component is sesame oil.
5. The method of claim 1, wherein the component is cotton seed oil.
6. The method of claim 1 further comprising placing the formulation into a dosage form for treating a tissue of a subject, the treating including inhibiting the onset of, or treating, an infection of the tissue.
7. The method of claim 6, wherein the tissue is a dermal tissue.
8. The method of claim 6, wherein the tissue is a mucosal tissue.
9. The method of claim 6, wherein the tissue is gastrointestinal tissue.
10. The method of claim 1 further comprising placing the formulation into a dosage form for treating a wounded tissue of a subject.
11. The method of claim 10, wherein the tissue is a dermal tissue.
12. The method of claim 10, wherein the tissue is a mucosal tissue.
13. The method of claim 10, wherein the tissue is gastrointestinal tissue.
14. The method of claim 1 further comprising placing the formulation into a dosage form for treating a tissue of a subject, the treating including inhibiting the onset of, or treating, an inflammation of the tissue.
15. The method of claim 14, wherein the tissue is a dermal tissue.
16. The method of claim 14, wherein the tissue is a mucosal tissue.
17. The method of claim 16, wherein the tissue is gastrointestinal tissue.
18. A method of preparing a formulation acceptable for oral administration having a pharmaceutically acceptable emulsion of a liquid extract of *Curcuma*, the method comprising:
    macerating at least a portion of a *Curcuma* root for an effective time in an at least substantially non-toxic extraction solvent that includes a component selected from the group consisting of sesame oil, liquid paraffin, glycerin, squalene, cotton seed oil, liquid-grade polyethylene glycol, isopropyl myristate, polysorbate 80, a sorbitan alkanoate, an ethoxylated sorbitan alkanoate, and combinations thereof;
    separating the extraction solvent from the portion of the macerated *Curcuma* root to create a liquid extract of *Curcuma*, the extract including curcumin;
    emulsifying the liquid extract; and,
    incorporating the emulsified liquid extract directly into the formulation for oral administration without removal of the extraction solvent, the carrier having the acute oral toxicity with the LD50 of at least 49,700 mg/kg which is at least substantially less toxic than ethanol.
19. The method of claim 18, wherein the extraction solvent comprises polyoxyethylene (20) sorbitan monooleate.
20. The method of claim 18, wherein the extraction solvent comprises isopropyl myristate.
21. The method of claim 18, wherein the emulsifying includes adding a pharmaceutically acceptable oil to the liquid extract to create the emulsion of the liquid extract.
22. The method of claim 18, wherein the emulsifying includes adding an emulgent to the liquid extract to create the emulsion of the liquid extract.
23. The method of claim 21, wherein the component is sesame oil.

24. The method of claim 21, wherein the component is cotton seed oil.

25. The method of claim 18 further comprising placing the formulation into a dosage form for treating an infection of a tissue of a subject, the treating including inhibiting the onset of, or treating, an infection of the tissue.

26. The method of claim 25, wherein the tissue is a dermal tissue.

27. The method of claim 25, wherein the tissue is a mucosal tissue.

28. The method of claim 25, wherein the tissue is gastrointestinal tissue.

29. The method of claim 18 further comprising placing the formulation into a dosage form for treating a wounded tissue of a subject.

30. The method of claim 29, wherein the tissue is a dermal tissue.

31. The method of claim 29, wherein the tissue is a mucosal tissue.

32. The method of claim 31, wherein the tissue is gastrointestinal tissue.

33. The method of claim 1 further comprising placing the formulation into a dosage form for treating a tissue of a subject, the treating including inhibiting the onset of, or treating, an infection of the tissue.

34. The method of claim 33, wherein the tissue is a dermal tissue.

35. The method of claim 33, wherein the tissue is a mucosal tissue.

36. The method of claim 35, wherein the tissue is gastrointestinal tissue.

\* \* \* \* \*